(12) United States Patent
Kaufmann

(10) Patent No.: US 6,174,679 B1
(45) Date of Patent: Jan. 16, 2001

(54) CIF150/HTAF$_{II}$150 IS NECESSARY FOR CELL CYCLE PROGRESSION

(75) Inventor: Joerg Kaufmann, Berkeley, CA (US)

(73) Assignee: Chiron Corporation, Emeryville, CA (US)

(*) Notice: Under 35 U.S.C. 154(b), the term of this patent shall be extended for 0 days.

(21) Appl. No.: 09/208,742

(22) Filed: Dec. 10, 1998

Related U.S. Application Data

(60) Provisional application No. 60/068,965, filed on Dec. 30, 1997.

(51) Int. Cl.$^7$ .............................. C12Q 1/68; C07H 21/04; A61K 48/00; C12N 15/00
(52) U.S. Cl. .............................. 435/6; 435/375; 435/91.1; 536/23.1; 536/24.3; 536/24.5; 530/300; 530/350
(58) Field of Search .............................. 435/6, 7.21, 91.1, 435/91.31, 91.4, 455, 471, 325, 366, 375, 320.1; 536/23.1, 24.1, 24.3, 24.5; 514/44; 530/300, 350, 387.1

(56) References Cited

FOREIGN PATENT DOCUMENTS

WO 94/17087    8/1994   (WO) .

OTHER PUBLICATIONS

Anderson, Nature 392/supp.: 25–30, Apr. 1998.*
Reynolds et al., Molecular Medicine Today, pp. 25–31, Jan. 1999.*
Wodnar–Filipowicz et al., EMBL Database, Accession No. K01334, *Proc. Natl. Acad. Sci. USA* 81:2295–2297, 1984.
Kaufmann et al., "CIF, an essential cofactor for TFIID–dependent inititator function," *Genes & Development* 10:873–886, 1996.
Kaufmann et al., "CIF 150, a Human Cofactor for Transcription Factor IID–Dependent Initiator Function," *Molecular And Cellular Biology* 18(1):233–239, 1998.
Marra et al., EMBL Database EMEST 19, Accession No. AA103510, Oct. 30, 1996.
Martinez et al., "Novel Cofactors and TFIIA Mediate Functional Core Promoter Selectivity by the Human TAF$_{II}$150–Containing TFIID Complex," *Molecular And Cellular Biology* 18(11):6571–6583, 1998.
Verrijzer et al., "Drosophila TAF$_{II}$150: Similarity to Yeast Gene TSM–1 and Specific Binding to Core Promoter DNA," *Science* 264:933–941, 1994.
Walker et al., "Transcription activation in cells lacking TAF$_{II}$s," *Nature* 383:185–188, 1996.
Wodnar–Filipowicz et al., EMBL Database, Accession No. K01334, Mar. 1, 1991.

\* cited by examiner

*Primary Examiner*—George C. Elliott
*Assistant Examiner*—M Schmidt
(74) *Attorney, Agent, or Firm*—Jane E. R. Potter; Kimberlin L. Morley; Robert P. Blackburn

(57) ABSTRACT

A human protein termed CIF150/hTAF$_{II}$150 recognizes and selects TATA-less core promoters for cell cycle specific genes. Thus, CIF150/hTAF$_{II}$150 plays an important and selective role in establishing gene expression patterns necessary for progression through the cell cycle. The CIF150/hTAF$_{II}$150 gene and its expression products can be used to alter the spatial or temporal patterns of mitosis or cell cycle progression of a human cell and to treat disorders involving alterations in the regulation of mitosis or cell cycle progression.

26 Claims, 11 Drawing Sheets

HeLa cells oligo Bx (reverse)      oligo B (antisense)

IMR-90 cells

400nM oligo B
27% G2M

400nM oligo Bx
9% G2M no oligo control
9% G2M

5' GTACCGAGCTCGGATCC N N N N N N CTCGAGCATGCATCTAG 3'

| | N | N | N | N | N | N | |
|---|---|---|---|---|---|---|---|
| G: | 8 | 10 | 37 | 0 | 36 | 6 | 3 |
| A: | 6 | 12 | 4 | 38 | 2 | 22 | 17 |
| T: | 11 | 10 | 2 | 6 | 2 | 5 | 12 |
| C: | 19 | 12 | 1 | 0 | 4 | 11 | 12 | n=44

CONSENSUS: Py X G A G A/C A/Py

Fig. 4C

CIF150/HTAF$_{II}$150 IS NECESSARY FOR CELL CYCLE PROGRESSION

This application claims the benefit of co-pending provisional application Ser. No. 60/068,965 filed Dec. 30, 1997, which is incorporated herein by reference.

TECHNICAL AREA OF THE INVENTION

The invention relates to the area of cell cycle progression. More particularly, the invention relates to proteins which regulate cell cycle progression.

BACKGROUND OF THE INVENTION

Alterations in the regulation of mitosis or cell cycle progression play an important role in diseases such as neoplasia and anemia. Manipulation of genes involved in regulating the cell cycle can be used to prevent or treat these diseases. Detections of mutations in cell-cycle regulatory genes can also be used to detect neoplastic cells and genetic predispositions to neoplasias. Thus, there is a need in the art for the identification of cell cycle regulator genes which can be used in methods of diagnosing, prognosing, and treating neoplasia and other diseases in humans and other mammals.

SUMMARY OF THE INVENTION

It is an object of the invention to provides reagents and methods for regulating mitosis or cell cycle progression in human cells and for treating disorders related to alterations in mitosis or cell cycle progression. These and other objects of the invention are provided by one or more of the embodiments described below.

One embodiment of the invention is an isolated and purified subgenomic polynucleotide which encodes a protein comprising an amino acid sequence which is at least 85% identical to the nucleotide sequence shown in SEQ ID NO:2. Percent identity is determined using a Smith-Waterman homology search algorithm using an affine gap search with a gap open penalty of 12 and a gap extension penalty of 1.

Another embodiment of the invention is an isolated and purified subgenomic polynucleotide which comprises at least 11 contiguous nucleotides selected from the nucleotide sequence shown in SEQ ID NO:1.

Yet another embodiment of the invention is a construct which comprises a promoter and a polynucleotide segment encoding a human CIF150/hTAF$_{II}$150 protein as shown in SEQ ID NO:2. The polynucleotide segment is located downstream from the promoter. Transcription of the polynucleotide segment initiates at the promoter.

Still another embodiment of the invention is a host cell comprising a construct. The construct comprises a promoter and a polynucleotide segment encoding a human CIF150/hTAF$_{II}$150 protein as shown in SEQ ID NO:2.

Another embodiment of the invention provides a homologously recombinant cell having incorporated therein a new transcription initiation unit. The new transcription initiation unit comprises an exogenous regulatory sequence, an exogenous exon, and a splice donor site. The transcription initiation unit is located upstream of a coding sequence of a CIF150/hTAF$_{II}$150 gene. The exogenous regulatory sequence directs transcription of the coding sequence of the CIF150/hTAF$_{II}$150 gene.

Even another embodiment of the invention provides a method to aid in the diagnosis or prognosis of neoplasia in a human. Expression of a first CIF150/hTAF$_{II}$150 gene in a first tissue of a human suspected of being neoplastic is compared with expression of a second CIF150/hTAF$_{II}$150 gene in a second tissue of a human which is normal. The second CIF150/hTAF$_{II}$150 gene has the coding sequence shown in SEQ ID NO:1. Increased expression of the first CIF150/hTAF$_{II}$150 relative to the second CIF150/hTAF$_{II}$150 gene indicates neoplasia in the first tissue.

Yet another embodiment of the invention provides a method to aid in the diagnosis or prognosis of neoplasia in a human. A human CIF150/hTAF$_{II}$150 gene, mRNA, or protein in a first tissue suspected of being neoplastic is compared with a second human CIF150/hTAF$_{II}$150 gene, mRNA, or protein in a second tissue which is normal. The second CIF150/hTAF$_{II}$150 gene has the coding sequence shown in SEQ ID NO:1. A difference between the first and second genes, mRNAs, or proteins in the second tissue indicates neoplasia in the first tissue.

Still another embodiment of the invention provides a method to aid in detecting a genetic predisposition to neoplasia in a human. A CIF150/hTAF$_{II}$150 gene, mRNA, or protein in a fetal tissue of a human is compared with a wild-type human CIF150/hTAF$_{II}$150 gene, mRNA, or protein. The wild-type CIF150/hTAF$_{II}$150 gene has the coding sequence shown in SEQ ID NO:1. A difference between the CIF150/hTAF$_{II}$150 gene, mRNA, or protein in the fetal tissue of the human and the wild-type human CIF150/hTAF$_{II}$150 gene, mRNA, or protein indicates a genetic predisposition to neoplasia in the human.

Even another embodiment of the invention provides a method of screening test compounds for the ability to interfere with the binding of a CIF130 protein to a CIF150/hTAF$_{II}$150 protein. A test compound is contacted with a CIF150/hTAF$_{II}$150-binding domain of a CIF130 protein and a CIF130-binding domain of a CIF150/hTAF$_{II}$150 protein. The CIF130 protein has the amino acid sequence shown in SEQ ID NO:4. The CIF150/hTAF$_{II}$150 protein has the amino acid sequence shown in SEQ ID NO:2. The CIF130-binding domain binds to the CIF150/hTAF$_{II}$150-binding domain in the absence of the test compound. The amount of at least one of the CIF130- or CIF150/hTAF$_{II}$150-binding domains which is bound or unbound is determined in the presence of the test compound. A test compound which decreases the amount of bound CIF130- or CIF150/hTAF$_{II}$150-binding domains or which increases the amount of unbound CIF130- and CIF150/hTAF$_{II}$150-binding domains is a potential inducer of mitosis or cell cycle progression.

Yet another embodiment of the invention provides a method of screening test compounds for the ability to interfere with the binding of a CIF130 protein to a CIF150/hTAF$_{II}$150 protein. A cell is contacted with a test compound. The cell comprises two fusion proteins. A first fusion protein comprises (1) a CIF150/hTAF$_{II}$150-binding domain of a CIF130 protein and (2) either a DNA binding domain or a transcriptional activating domain. A second fusion protein comprises a CIF130-binding domain of a CIF150/hTAF$_{II}$150 protein. The CIF130 protein has the amino acid sequence shown in SEQ ID NO:4. The CIF150/hTAF$_{II}$150 protein has the amino acid sequence shown in SEQ ID NO:2. The CIF130-binding domain binds to the CIF150/hTAF$_{II}$150-binding domain. If the first fusion protein comprises a DNA binding domain, then the second fusion protein comprises a transcriptional activating domain. If the first fusion protein comprises a transcriptional activating domain, then the second fusion protein comprises a DNA binding domain. The interaction of the first and second fusion proteins reconstitutes a sequence-specific transcription activating factor. The cell also comprises a reporter gene comprising a DNA sequence to which the DNA binding domain specifically binds. Expression of the reporter gene is measured. A test compound which decreases the expression of the reporter gene is a potential inducer of mitosis or cell cycle progression.

Even another embodiment of the invention provides a method of increasing expression of a gene. A promoter region of the gene is contacted with a CIF150/hTAF$_{II}$150 protein as shown in SEQ ID NO:2. The promoter region of the gene comprises a CIF150/hTAF$_{II}$150 binding element. The CIF150/hTAF$_{II}$150 binding element comprises a nucleotide sequence 5'-Py X G A G A/C A/Py-3' (SEQ ID NO:7). Expression of the gene is thereby increased.

Still another embodiment of the invention is an antisense oligonucleotide as shown in SEQ ID NO:5.

Yet another embodiment of the invention provides an isolated and purified subgenomic polynucleotide which comprises 5'-Py X G A G A/C A/Py-3' (SEQ ID NO:7).

The present invention thus provides the art with reagents and methods of affecting human mitosis or cell cycle progression and treating disorders associated with alterations in mitosis or cell cycle progression.

BRIEF DESCRIPTION OF THE DRAWINGS

FIG. 1A. Analysis of the cell cycle of HeLa cells 36 hours after transfection with the CIF150/hTAF$_{II}$150 specific antisense oligomer B or the oligomer Bx (reverse sequence). Concentrations of the oligomers are indicated. The proportion of G$_2$/M cells (dark cross-hatch) remained the same for the three concentrations of oligomer Bx, whereas the proportion of G$_2$/M cells increased as the concentration of antisense oligomer B was raised from 100 mM to 300 mM. FIG. 1B. Cell cycle analysis of IMR 90 cells after 36 hours of oligomer treatment. In the presence of oligomer Bx, the proportion of G$_2$/M cells, 9%, was the same as for the control IMR—90 cells, whereas in the presence of antisense oligomer B, the proportion of cells in G$_2$/M was 27%. FIG. 1C. Total RNA derived from HeLa cells treated with oligomer B or Bx analyzed by quantitative RT-PCR (lanes 1 to 6, 100, 200, 300 nM oligomer B and Bx) and Northern blot analysis (lanes 7 to 10) using CIF150/hTAF$_{II}$150 and β-actin-specific primers or $^{32}$P-labeled cDNA probes. FIG. 1D. HeLa cell extracts from different time points after antisense oligomer treatment analyzed by immunoblotting for the decrease of CIF150/hTAF$_{II}$150 protein. A control nuclear extract (lane 1) and a molecular size marker (lane 2) were loaded. FIG. 1E. Cyclin B1 protein expression decreases after CIF150/hTAF$_{II}$150 antisense treatment of HeLa cells (left panel). FIG. 1F. PCR display identifies genes which are transcriptionally dependent on CIF150/hTAF$_{II}$150. Total RNA was prepared 24 hours (lane 1 and 2) or 36 hours (lane 3 and 4) after oligomer transfection.

FIG. 2A. Quiescent BALB/c 3T3 cells were stimulated to undergo cell cycle traverse by serum addition. Extracts derived from cells at times indicated above were assayed for CIF150/hTAF$_{II}$150, cyclin B1, cyclin A, and cyclin E by immunoblot. FIG. 2B. HeLa cells were assayed for CIF150/hTAF$_{II}$150 and cyclin B1 expression after synchronization for 48 hours by serum deprivation. FIG. 2C. Nuclear extracts of HeLa cells harvested at different time points after release from a double thymidine block were used for in vitro transcription assays using promoter with (odd numbered lanes) and without functional TdT Inr (even numbered lanes). Nuclear extracts were standardized by protein concentration.

FIG. 3A. Purified CIF150/hTAF$_{II}$150 was visualized after SDS-PAGE by silver staining. FIG. 3B. CIF150/hTAF$_{II}$150 is required for cyclin B1 and cyclin A transcription but not for IgH and CMV transcription. In vitro transcription was performed using CIF150/hTAF$_{II}$150 depleted nuclear extracts (lane 1) or in combination with increasing amounts of recombinant CIF150/hTAF$_{II}$150 protein (lane 2 to 4). FIG. 3C. Cotransfection of increasing amounts of CIF150/hTAF$_{II}$150 expression plasmid with cyclin B1, cyclin A, CMV, and Fos promoter driven luciferase reporter constructs. The values are represent the average of four experiments +/− standard deviation.

FIGS. 4A–4D. CIF150/hTAF$_{II}$150 has sequence-specific binding activity. FIG. 4A. CIF150/hTAF$_{II}$150 binding site selection. FIG. 4B. Addition of anti-CIF150/hTAF$_{II}$150 (lane 4) but not preimmune serum (lane 3) supershifted the retarded band. FIG. 4C. Consensus CIF150/hTAF$_{II}$150 binding element (CBE). FIG. 4D. Point mutational analysis of the CIF150/hTAF$_{II}$150 binding element using gel shift experiments.

DETAILED DESCRIPTION OF THE PREFERRED EMBODIMENTS

Figure 1A:
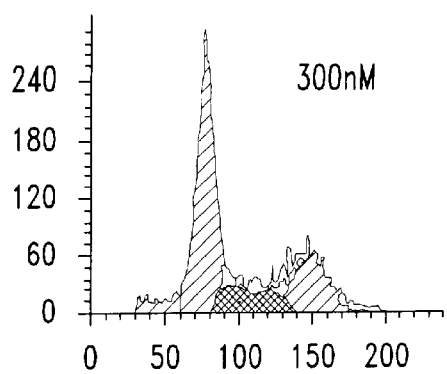
FIGS. 1A–1F. Functional knock out of CIF150/hTAF$_{II}$150 protein leads to cell cycle arrest in G$_2$/M and reduced gene expression of cyclin B1.
Figure 1A:
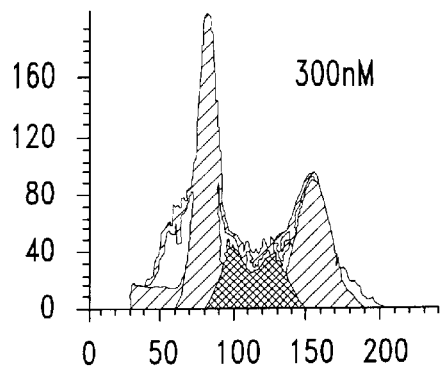
Figure 1A:
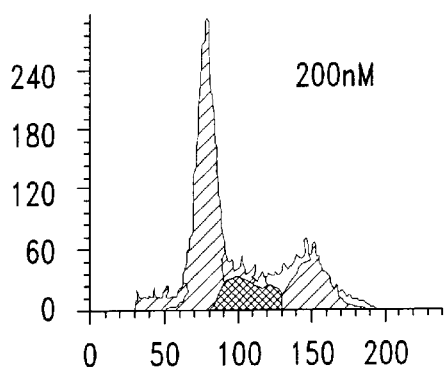
Figure 1A:
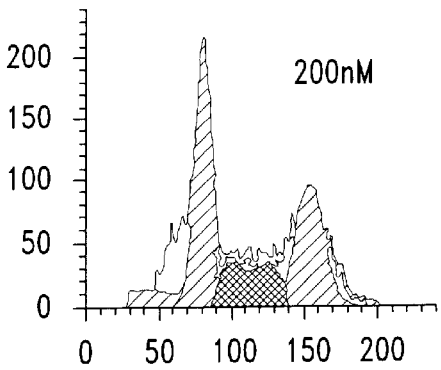
Figure 1A:
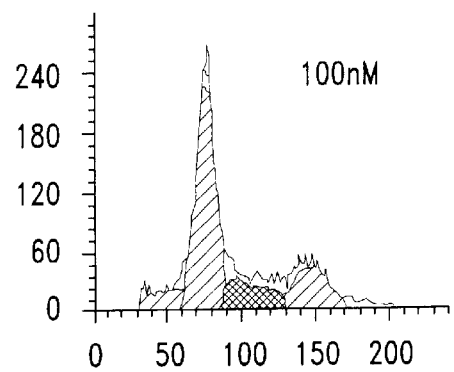
Figure 1A:
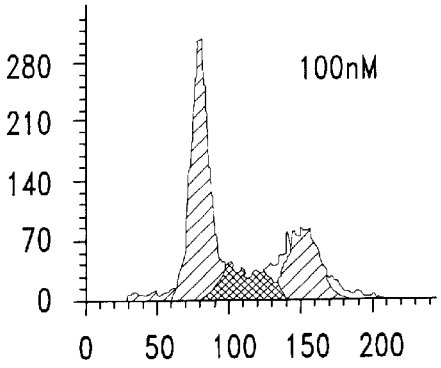

It is a discovery of the present invention that a protein termed CIF150/hTAF$_{II}$150 recognizes and selects TATA-less core promoters for cell cycle specific genes. Thus, CIF150/hTAF$_{II}$150 plays an important and selective role in establishing gene expression patterns necessary for progression through the cell cycle. Through manipulation of CIF150/hTAF$_{II}$150 expression, the present invention provides reagents and methods for affecting mitosis or cell cycle progression of human cells and for treating disorders associated with alterations in mitosis or cell cycle progression.

CIF150/hTAF$_{II}$150 is a necessary positive transcriptional regulator of cell cycle progression through G$_2$/M. CIF150/hTAF$_{II}$150 is an essential cofactor for TF$_{II}$D-dependent transcription from promoters containing initiator elements, such as the adenovirus major late promoter. CIF150/hTAF$_{II}$150 directly interacts with the transcription factor hTAF$_{II}$135 and stabilizes TF$_{II}$D binding to RNA polymerase II core promoters and can stimulate expression of cell cycle-specific genes such as cyclin A and B1. The promoters of such genes contain a CIF150/hTAF$_{II}$150 binding element which comprises a CIF150/hTAF$_{II}$150 binding site, 5'-Py X G A G A/C A/Py-3' (SEQ ID NO:7).

CIF150/hTAF$_{II}$150 binds to and is negatively regulated by a 130 kD polypeptide, CIF130, which has sequence homology to ATP-dependent RNA helicases (DEAD-box proteins) implicated in the control of mitosis in *Schizosaccharomyces pombe*. A nucleotide sequence encoding CIF130 is shown in SEQ ID NO:3. The amino acid sequence of CIF130 is shown in SEQ ID NO:4.

Human CIF150/hTAF$_{II}$50 protein has the amino acid sequence shown in SEQ ID NO:2. Protein variants of CIF150/hTAF$_{II}$150 protein can also have CIF150/hTAF$_{II}$150 activity. Biologically active CIF150/hTAF$_{II}$150 variants can be naturally or non-naturally occurring. Naturally occurring CIF150/hTAF$_{II}$150 variants are those which are found in humans or other species and which comprise amino acid sequences which are substantially identical to the amino acid sequence shown in SEQ ID NO:2. Non-naturally occurring CIF150/hTAF$_{II}$150 variants which retain substantially the same biological activities as CIF150/hTAF$_{II}$150 or naturally occurring CIF150/hTAF$_{II}$150 variants can be constructed in the laboratory.

Preferably, naturally or non-naturally occurring protein biologically active CIF150/hTAF$_{II}$50 variants have amino acid sequences which are at least 65%, 75%, 85%, 90%, or 95% identical to the amino acid sequence shown in SEQ ID NO:2 and have similar biological properties, including the ability to bind to the CIF150/hTAF$_{II}$150 binding element, to permit mitosis, to activate TATA-less core promoters, and to bind to CIF130. More preferably, the molecules are at least 98% or 99% identical. Percent sequence identity between the CIF150/hTAF$_{II}$150 protein shown in SEQ ID NO:2 and a biologically active CIF150/hTAF$_{II}$150 variant is determined using the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482–489.

Guidance in determining which amino acid residues may be substituted, inserted, or deleted without abolishing biological or immunological activity of CIF150/hTAF$_{II}$150 may be found using computer programs well known in the art, such as DNASTAR software. Preferably, the amino acid changes in biologically active CIF150/hTAF$_{II}$150 variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting CIF150/hTAF$_{II}$150 variant, especially if the replacement does not involve an amino acid at the CIF130-binding site of CIF150/hTAF$_{II}$150 or the site at which CIF150/hTAF$_{II}$150 binds to the CIF150/hTAF$_{II}$150 binding element. Properties and functions of CIF150/hTAF$_{II}$150 variants are of the same type as a CIF150/hTAF$_{II}$150 protein having the amino acid sequence shown in SEQ ID NO:2, although the properties and functions may differ in degree. Whether an amino acid change results in a CIF150/hTAF$_{II}$150 protein or polypeptide variant which can function as the CIF150/hTAF$_{II}$150 protein disclosed herein can readily be determined. For example, the ability of a CIF150/hTAF$_{II}$150 variant to bind to the CIF150/hTAF$_{II}$150 binding element can be tested using in vitro DNA binding assays, as taught in Kaufmann & Smale, 1994, *Genes Devel.* 8:821–29 and Kaufmann et al., 1996, *Genes Devel.* 10:873–86. The ability of a CIF150/hTAF$_{II}$150 protein or polypeptide variant to induce mitosis or cell cycle progression can be assayed as described below.

CIF150/hTAF$_{II}$150 polypeptides contain less than full-length CIF150/hTAF$_{II}$150. For example, CIF150/hTAF$_{II}$150 polypeptides contain at least 5, 6, 8, 10, 12, 20, 25, 50, 75, 100, 200, 300, 400, 500, 600, 700, 800, 900, 1000, 1250, or 1300 or more amino acids of a CIF150/hTAF$_{II}$150 protein or biologically active variant in the same primary order as found in a CIF150/hTAF$_{II}$150 protein or variant obtained from a natural source. Polypeptide molecules having substantially the same amino acid sequence as CIF150/hTAF$_{II}$150 but possessing minor amino acid substitutions which do not substantially affect the ability of the CIF150/hTAF$_{II}$150 polypeptide variants to interact with CIF150/hTAF$_{II}$150-specific molecules, such as CIF130 or antibodies which specifically bind to CIF150/hTAF$_{II}$150, are within the definition of CIF150/hTAF$_{II}$150. CIF130 variants include glycosylated forms, aggregative conjugates with other molecules, and covalent conjugates with unrelated chemical moieties.

Truncations or deletions of regions which do not affect the properties or functions of CIF150/hTAF$_{II}$150 described above are also biologically active variants of CIF150/hTAF$_{II}$150. Covalent variants can be prepared by linkage of functionalities to groups which are found in the amino acid chain or at the N- or C-terminal residue, as is known in the art.

A subset of mutants, called muteins, is a group of polypeptides in which neutral amino acids, such as serines, are substituted for cysteine residues which do not participate in disulfide bonds. These mutants may be stable over a broader temperature range than native CIF150/hTAF$_{II}$150. See Mark et al., U.S. Pat. No. 4,959,314.

Naturally occurring CIF150/hTAF$_{II}$150 proteins or polypeptides can be purified from human cells or cell lines, such as HeLa or NIH 3T3 cells, by methods known in the art. CIF150/hTAF$_{II}$150 copurifies with CIF130; thus, the initial purification steps for each protein are the same. CIF150/hTAF$_{II}$150 can be conveniently purified from IIeLa cell extracts (Dignam et al., 1983, *Nucl. Acids Res.* 11:1475–89) using Ni affinity chromatography. For Ni affinity purification, the 0.1 M KCl flowthrough fraction of a DEAE-Sephacel column is applied to a Mono Q column and eluted with a linear KCl gradient (40 ml; 0.1 to 1 M). The CIF130/CIF150/hTAF$_{II}$150-containing fractions are pooled and dialyzed against buffer A (20 mM HEPES, pH 7.9, 1 mM EDTA, 3 mM dithiothreitol, 1 mM phenylmethylsulfonyl fluoride, 20% glycerol) containing 0.1 M KCl. These fractions are supplemented with imidazole (final concentration, 20 mM in buffer A) and applied to a Ni-nitrilotriacetic acid (NTA)-agarose column (Qiagen). After being washed with 10 column volumes each of 20 mM imidazole and 35 mM imidazole, bound proteins are eluted with 100 mM imidazole.

Protein fractions can be tested for CIF150/hTAF$_{II}$150 activity as described in Kaufmann et al., 1996. Purified CIF130 and CIF150/hTAF$_{II}$150 proteins can be visualized by sodium dodecyl sulfate-6% polyacrylamide gel electrophoresis, followed by silver staining. CIF150/hTAF$_{II}$150 can be separated from CIF130 by excising the CIF150/hTAF$_{II}$150-containing band from the SDS gel and eluting the CIF150/hTAF$_{II}$150 protein, as is known in the art. A preparation of isolated and purified CIF150/hTAF$_{II}$150 protein is at least 80% pure; preferably, the preparations are at least 90%, 95%, or 99% pure.

CIF150/hTAF$_{II}$150 proteins and polypeptides can also be produced by recombinant DNA methods or by synthetic chemical methods. For production of recombinant CIF150/hTAF$_{II}$150 proteins or polypeptides, coding sequences selected from the CIF150/hTAF$_{II}$150 nucleotide sequence shown in SEQ ID NO:1 can be expressed in known prokaryotic or eukaryotic expression systems (see below). To avoid non-specific T7 RNA polymerase transcription in functional assays, in vitro-translated CIF150/hTAF$_{II}$150 can be purified with Ni-NTA-agarose as described above (100 mM imidazole eluate) and concentrated with a Centricon 30 concentrator (Amicon). Bacterial, yeast, insect, or mammalian expression systems can be used, as is known in the art. Alternatively, synthetic chemical methods, such as solid phase peptide synthesis, can be used to synthesize CIF150/hTAF$_{II}$150 protein or polypeptides. CIF150/hTAF$_{II}$150 biologically active variants can be similarly produced.

Fusion proteins comprising at least six contiguous CIF150/hTAF$_{II}$150 amino acids can also be constructed. Human CIF150/hTAF$_{II}$150 fusion proteins are useful for generating antibodies against CIF150/hTAF$_{II}$150 amino acid sequences and for use in various assay systems, For example, CIF150/hTAF$_{II}$150 fusion proteins can be used to identify proteins which interact with CIF150/hTAF$_{II}$150 protein and influence its ability to affect transcription. Physical methods, such as protein affinity chromatography, or library-based assays for protein-protein interactions, such as the yeast two-hybrid or phage display systems, can be used for this purpose. Such methods are well known in the art and can also be used as drug screens, as described below.

A CIF150/hTAF$_{II}$150 fusion protein comprises two protein segments fused together by means of a peptide bond. The first protein segment consists of at least 5, 6, 8, 10, 12, 20, 25, 50, 75, 100, 200, 300, 400, 500, 600, 700, 800, 900, 1000, 1250, or 1300 contiguous amino acids of a CIF150/hTAF$_{II}$150 protein. The amino acids can be selected from the amino acid sequence shown in SEQ ID NO:2 or from a biologically active variant of that sequence. The first protein segment can also be a full-length CIF150/hTAF$_{II}$150 protein. The first protein segment can be N-terminal or C-terminal, as is convenient.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

CIF150/hTAF$_{II}$150 fusion proteins can be made by covalently linking the first and second protein segments or by standard procedures in the art of molecular biology. Recombinant DNA methods can be used to prepare CIF150/hTAF$_{II}$150 fusion proteins, for example, by making a DNA construct which comprises coding sequences selected from SEQ ID NO:1 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated and purified CIF150/hTAF$_{II}$150 proteins, polypeptides, variants, or fusion proteins can be used as immunogens, to obtain a preparation of antibodies which specifically bind to a CIF150/hTAF$_{II}$150 protein. The antibodies can be used, inter alia, to detect wild-type CIF150/hTAF$_{II}$150 proteins in human tissue and fractions thereof. The antibodies can also be used to detect the presence of mutations in the CIF150/hTAF$_{II}$150 gene which result in under- or over-expression of the CIF150/hTAF$_{II}$150 protein or in expression of a CIF150/hTAF$_{II}$150 protein with altered size or electrophoretic mobility.

Antibodies which specifically bind to epitopes of CIF150/hTAF$_{II}$150 proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to CIF150/hTAF$_{II}$150 epitopes do not detect other proteins in immunochemical assays and can immunoprecipitate CIF150/hTAF$_{II}$150 protein or polypeptides from solution.

CIF150/hTAF$_{II}$150-specific antibodies specifically bind to epitopes present in a CIF150/hTAF$_{II}$150 protein having the amino acid sequence shown in SEQ ID NO:2 or to biologically active variants of that sequence. Typically, at least 6, 8, 10, or 12 contiguous amino acids are required to form an epitope. However, epitopes which involve non-contiguous amino acids may require more, e.g., at least 15, 25, or 50 amino acids. Preferably, CIF150/hTAF$_{II}$150 epitopes are not present in other human proteins. One such preparation of anti-CIF150/hTAF$_{II}$150 antibodies are polyclonal antibodies raised against an N-terminal peptide of CIF150/hTAF$_{II}$150, such as MNRKKGDKGF (amino acids 11–20 of SEQ ID NO:2) or MNRKKGDKGFESPRP (amino acids 11–25 of SEQ ID NO:2).

Epitopes of CIF150/hTAF$_{II}$150 which are particularly antigenic can be selected, for example, by routine screening of CIF150/hTAF$_{II}$150 polypeptides for antigenicity or by applying a theoretical method for selecting antigenic regions of a protein to the amino acid sequence shown in SEQ ID NO:2. Such methods are taught, for example, in Hopp and Wood, *Proc. Natl. Acad. Sci. U.S.A.* 78, 3824–28 (1981), Hopp and Wood, *Mol. Immunol.* 20, 483–89 (1983), and Sutcliffe et al., *Science* 219, 660–66 (1983).

Any type of antibody known in the art can be generated to bind specifically to CIF150/hTAF$_{II}$150 epitopes. For example, preparations of polyclonal and monoclonal antibodies can be made using standard methods which are well known in the art. Similarly, single-chain antibodies can also be prepared. Single-chain antibodies which specifically bind to CIF150/hTAF$_{II}$150 epitopes can be isolated, for example, from single-chain immunoglobulin display libraries, as is known in the art. The library is "spanned" against CIF150/hTAF$_{II}$150 amino acid sequences, and a number of single chain antibodies which bind with high-affinity to different epitopes of CIF150/hTAF$_{II}$150 protein can be isolated. Hayashi et al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J. Cancer Prev.* 5:507–11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159–63. Construction of bivalent, bispecific single-chain antibodies is taught inter alia in Mallender and Voss, 1994, *J. Biol. Chem.* 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Monoclonal and other antibodies can also be "humanized" in order to prevent a patient from mounting an immune response against an antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to CIF150/hTAF$_{II}$150 epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which a CIF150/hTAF$_{II}$150 protein, polypeptide, biologically active variant, or fusion protein is bound. The bound antibodies can then be eluted from the column, using a buffer with a high salt concentration.

CIF150/hTAF$_{II}$150-specific binding polypeptides other than antibodies can also be generated. CIF150/hTAF$_{II}$150-specific binding polypeptides are polypeptides which bind with CIF150/hTAF$_{II}$150 or its variants and which have a measurably higher binding affinity for CIF150/hTAF$_{II}$150 and polypeptide derivatives of CIF150/hTAF$_{II}$150 than for other polypeptides tested for binding. Higher affinity by a factor of 10 is preferred, more preferably a factor of 100. Such polypeptides can be identified, for example, using the yeast two-hybrid system.

The coding region of the human CIF150/hTAF$_{II}$150 gene has the nucleotide sequence shown in SEQ ID NO:1. The complement of the nucleotide sequence shown in SEQ ID NO:1 consists of a contiguous nucleotide sequence which forms Watson-Crick base pairs with the contiguous nucleotide sequence shown in SEQ ID NO:1.

CIF150/hTAF$_{II}$150 subgenomic polynucleotides can comprise at least 11, 20, 25, 30, 35, 40, 45, 50, 55, 60, 67, 70, 75, 100, 125, 150, 200, 250, 300, 400, 500, 750, 1000, 1250, 1500, 1750, 2000, 2500, 3000, 3500, or 3900 or more contiguous nucleotides selected from the nucleotide sequence shown in SEQ ID NO:1 or its complement. Subgenomic polynucleotides contain less than a whole chromosome and are preferably intron-free.

The complement of the nucleotide sequence shown in SEQ ID NO:1 can be used provide CIF150/hTAF$_{II}$150 antisense oligonucleotides. CIF150/hTAF$_{II}$150 subgenomic polynucleotides also include polynucleotides which encode CIF150/hTAF$_{II}$150-specific single-chain antibodies, ribozymes, and biologically active or altered CIF150/hTAF$_{II}$150 variants.

Degenerate nucleotide sequences encoding amino acid sequences of CIF150/hTAF$_{II}$150 protein or biologically active CIF150/hTAF$_{II}$150 variants, as well as homologous nucleotide sequences which are at least 65%, 75%, 85%, 90%, 95%, 96%, 97%, 98%, or 99% identical to the nucleotide sequence shown in SEQ ID NO:1, are also CIF150/hTAF$_{II}$150 subgenomic polynucleotides. Percent sequence identity between the nucleotide sequence of SEQ ID NO:1 and a putative homologous or degenerate CIF150/hTAF$_{II}$150 nucleotide sequence is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequence shown in SEQ ID NO:1 or its complement with at most 1, 2, 3, 4, 5, 10, 15, 20, 25, 30, or 35% basepair mismatches are also CIF150/hTAF$_{II}$150 subgenomic polynucleotides of the invention. For example, using the following wash conditions—2×SSC (0.3 M sodium chloride, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each--homologous CIF150/hTAF$_{II}$150 sequences can be identified which contain at most about 25–30% basepair mismatches with SEQ ID NO:1 or its complement. More preferably, homologous nucleic acid strands contain 15–25% basepair mismatches, even more preferably 5–15% basepair mismatches.

Species homologs of CIF150/hTAF$_{II}$150 subgenomic polynucleotides of the invention can also be identified by making suitable probes or primers and screening cDNA expression libraries from other species, such as mice, monkeys, yeast, or bacteria, as well as human CDNA expression libraries. It is well known that the $T_m$ of a double-stranded DNA decreases by 1–1.5° C. with every 1% decrease in homology (Bonner et al., *J. Mol. Biol.* 81, 123 (1973). Homologous CIF150/hTAF$_{II}$150 human polynucleotides or CIF150/hTAF$_{II}$150 polynucleotides of other species can therefore be identified, for example, by hybridizing a putative homologous CIF150/hTAF$_{II}$150 polynucleotide with a polynucleotide having the nucleotide sequence of SEQ ID NO:1 to form a test hybrids, comparing the melting temperature of the test hybrid with the melting temperature of a hybrid comprising a polynucleotide having SEQ ID NO:1 and a polynucleotide which is perfectly complementary to SEQ ID NO:1, and calculating the number or percent of basepair mismatches within the test hybrid.

Nucleotide sequences which hybridize to the coding sequence shown in SEQ ID NO:1 or its complement following stringent hybridization and/or wash conditions are also CIF150/hTAF$_{II}$150 subgenomic polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions, a combination of temperature and salt concentration should be chosen that is approximately 12–20° C. below the calculated T$_m$ of the hybrid under study. The T$_m$ of a hybrid between the CIF150/hTAF$_{II}$150 sequence shown in SEQ ID NO:1 and a polynucleotide sequence which is 65%, 75%, 85%, 90%, 95%, 96%, 97%, 98%, or 99% identical to SEQ ID NO:1 can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\%G+C) - 0.63(\%formamide) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

CIF150/hTAF$_{II}$150 subgenomic polynucleotides can be isolated and purified free from other nucleotide sequences using standard nucleic acid purification techniques. For example, restriction enzymes and probes can be used to isolate polynucleotide fragments which comprise nucleotide sequences encoding a CIF150/hTAF$_{II}$150 protein or variant. Isolated and purified subgenomic polynucleotides are in preparations which are free or at least 90% free of other molecules.

Complementary DNA (cDNA) molecules which encode CIF150/hTAF$_{II}$150 proteins are also CIF150/hTAF$_{II}$150 subgenomic polynucleotides of the invention. CIF150/hTAF$_{II}$150 cDNA molecules can be made with standard molecular biology techniques, using CIF150/hTAF$_{II}$150 mRNA as a template. CIF150/hTAF$_{II}$150 cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize CIF150/hTAF$_{II}$150 subgenomic polynucleotide molecules of the invention. The degeneracy of the genetic code allows alternate nucleotide sequences to be synthesized which will encode a CIF150/hTAF$_{II}$150 protein having the amino acid sequence shown in SEQ ID NO:2 or a biologically active variant of that sequence. All such nucleotide sequences are within the scope of the present invention.

The invention also provides polynucleotide probes which can be used to detect CIF150/hTAF$_{II}$150 sequences, for example, in hybridization protocols such as Northern or Southern blotting or in situ hybridization. Polynucleotide probes of the invention comprise at least 12, 13, 14, 15, 16, 17, 18, 19, 20, 30, or 40 or more contiguous nucleotides selected from SEQ ID NO:1. Polynucleotide probes of the invention can comprise a detectable label, such as a radioisotopic, fluorescent, enzymatic, or chemiluminescent label.

Purified and isolated CIF150/hTAF$_{II}$150 subgenomic polynucleotides can be used as primers to obtain additional copies of the polynucleotides or as probes for identifying wild-type and mutant CIF150/hTAF$_{II}$150 coding sequences. CIF150/hTAF$_{II}$150 subgenomic polynucleotides can also be used to express CIF150/hTAF$_{II}$150 mRNA, protein, polypeptides, fusion proteins and the like and to generate CIF150/hTAF$_{II}$150 antisense oligonucleotides and ribozymes.

CIF150/hTAF$_{II}$150 subgenomic polynucleotide comprising CIF150/hTAF$_{II}$150 coding sequences can be used in a construct, such as an RNA or DNA construct. A CIF150/hTAF$_{II}$150 construct can be an expression construct, which can be used to express all or a portion of a CIF150/hTAF$_{II}$150 protein in a host cell. Host cells comprising CIF150/hTAF$_{II}$150 expression constructs can be prokaryotic or eukaryotic. Preferably, the CIF150/hTAF$_{II}$150 subgenomic polynucleotide is inserted into an expression plasmid (for example, the Ecdyson system, pIND, In Vitro Gene).

A variety of host cells are available for use in bacterial, yeast, insect, and human expression systems and can be used to express CIF150/hTAF$_{II}$150 expression constructs (see below). Expression constructs can be introduced into host cells using any technique known in the art. These techniques include transferrin-polycation-mediated DNA transfer, transfection with naked or encapsulated nucleic acids, liposomemediated cellular fusion, intracellular transportation of DNA-coated latex beads, protoplast fusion, viral infection, electroporation, "gene gun," and calcium phosphatemediated transfection.

A CIF150/hTAF$_{II}$150 expression construct comprises a promoter which is functional in the particular host cell selected. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of a CIF150/hTAF$_{II}$150 protein, biologically active variant, fusion protein, antibody, or ribozyme. The polynucleotide segment is located downstream from the promoter. Transcription of the polynucleotide segment initiates at the promoter. The expression construct can be linear or circular and can contain sequences, if desired, for autonomous replication.

CIF150/hTAF$_{II}$150 subgenomic polynucleotides can be propagated in vectors and cell lines using techniques well known in the art. CIF150/hTAF$_{II}$150 subgenomic polynucleotides can be on linear or circular molecules. They can be on autonomously replicating molecules or on molecules without replication sequences. They can be regulated by their own or by other regulatory sequences, as are known in the art.

Expression systems in bacteria include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. USA* (1983) 80: 21–25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202:302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell.*

*Biol.* (1985) 5: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 2: 205–221, Yelton et al., *Proc. Natl. Acad. Sci. USA* (1984) 81: 1470–1474, Kelly and Hynes, *EMBO J.* (1985) 4: 475479; EP 244,234, and WO 91/00357.

Expression of CIF150/hTAF$_{II}$150 subgenomic polynucleotides in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad. Sci. USA* (1985) 82: 8404, Miyajima et al., *Gene* (1987) 58: 273; and Martin et al., DNA (1988) 7.99. Numerous baculoviral strains and variants and corresponding permissive insect host cells from hosts are described in Luckow et al., *Bio/Technology* (1988) 6: 47–55, Miller et al., in GENETIC ENGINEERING (Setlow, J. K. et al. eds.), Vol. 8 (Plenum Publishing, 1986), pp. 277–279, and Maeda et al., *Nature*, (1985) 315: 592–594.

Mammalian expression of CIF150/hTAF$_{II}$150 subgenomic polynucleotides can be achieved as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44; Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. RE 30,985.

Polynucleotides of the invention can also be used in gene delivery vehicles, for the purpose of delivering a CIF150/hTAF$_{II}$150 mRNA or oligonucleotide (either with the sequence of native CIF150/hTAF$_{II}$150 mRNA or its complement), full-length CIF150/hTAF$_{II}$150 protein, CIF150/hTAF 150 fusion protein, CIF150/hTAF 150 polypeptide, or CIF150/hTAF$_{II}$150-specific ribozyme or single-chain antibody, into a cell preferably a eukaryotic cell. According to the present invention, a gene delivery vehicle can be, for example, naked plasmid DNA, a viral expression vector comprising a CIF150/hTAF$_{II}$150 polynucleotide, or a CIF150/hTAF$_{II}$150 polynucleotide in conjunction with a liposome or a condensing agent.

In one embodiment of the invention, the gene delivery vehicle comprises a promoter and a CIF150/hTAF$_{II}$150 polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A CIF150/hTAF$_{II}$150 gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the CIF150/hTAF$_{II}$150 gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993; U.S. Pat. No. 4,777,127, GB 2,200,651, EP 0,345,242 and WO91/02805.

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliff et al., *J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et al., *J. Vir.* 67:4722, 1993; and Yantchev *Neoplasma* 26:397, 1979), Gross (ATCC No. VR-590), Kirsten (Albino et al., *J. Exp. Med.* 164:1710, 1986), Harvey sarcoma virus (Manly et al., *J. Vir.* 62:3540, 1988; and Albino et al., *J. Exp. Med.* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; and Albino et al., *J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral CIF150/hTAF$_{II}$150 gene delivery vehicles given the disclosure provided herein and standard recombinant techniques (e.g., Sambrook et al., MOLECULAR CLONING: A LABORATORY MANUAL, 2d ed., 1989, and Kunkle, *Proc. Natl. Acad. Sci. U.S.A.* 82:488, 1985) known in the art. Portions of retroviral CIF150/hTAF$_{II}$150 expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 07/800,921, filed Nov. 29, 1991). Recombinant retroviruses can be produced which direct the site-specific integration of the recombinant retroviral genome into specific regions of the host cell DNA. Such site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, Biotechniques 6:616–627, 1988, and Rosenfeld el al., Science 252:431–434, 1991, WO 93/07283, WO 93/06223, and WO 93/07282).

A CIF150/hTAF$_{II}$150 gene delivery vehicle can also be a recombinant adenoviral gene delivery vehicle. Such vehicles can be readily prepared and utilized given the disclosure provided herein (see Berkner, Biotechniques 6:616, 1988, and Rosenfeld et al., Science 252:431, 1991, WO 93/07283, WO 93/06223, and WO 93/07282). Adeno-associated viral CIF150/hTAF$_{II}$150 gene delivery vehicles can also be constructed and used to deliver CIF150/hTAF$_{II}$150 amino acids or nucleotides. The use of adeno-associated viral gene delivery vehicles in vitro is described in Chatterjee et al., Science 258: 1485–1488 (1992), Walsh et al., Proc. Nat'l. Acad. Sci. 89: 7257–7261 (1992), Walsh et al., J. Clin. Invest. 94: 1440–1448 (1994), Flotte et al., J. Biol. Chem. 268: 3781–3790 (1993), Ponnazhagan et al., J. Exp. Med. 179: 733–738 (1994), Miller et al., Proc. Nat'l Acad. Sci. 91: 10183–10187 (1994), Einerhand et al., Gene Ther. 2: 336–343 (1995), Luo et al., Exp. Hematol. 23: 1261–1267 (1995), and Zhou et al., Gene Therapy 3: 223–229 (1996). In vivo use of these vehicles is described in Flotte et al., Proc. Nat'l Acad. Sci. 90: 10613–10617 (1993), and Kaplitt et al., Nature Genet. 8:148–153 (1994).

In another embodiment of the invention, a CIF150/hTAF$_{II}$150 gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for CIF150/hTAF$_{II}$150 polynucleotides. Alpha viruses are described in WO 94/21792, WO 92/10578 and WO 95/07994. Several different alphavirus gene delivery vehicle systems can be constructed and used to deliver CIF150/hTAF$_{II}$150 polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis non-structural proteins, a viral junction region inactivated so as to prevent fragment transcription, and a Sindbis RNA polymerase recognition sequence. Optionally, the viral junction region can be modified so that polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the polynucleotide and a second viral junction region which has been modified such that polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al., Nature 339:385, 1989, and Sabin et al., J. Biol. Standardization 1:115,1973) (ATCC VR-58); rhinovirus (Arnold et al., J. Cell. Biochem. L401, 1990) (ATCC VR-1110); pox viruses, such as canary pox virus or vaccinia virus (Fisher-Hoch et al., Proc. Natl. Acad. Sci. USA. 86:317, 1989; Flexner et al., Ann. N.Y. Acad. Sci. 569:86, 1989; Flexner et al., Vaccine 8:17, 1990; U.S. Pat. No. 4,603,112 and U.S. Pat. No. 4,769,330; WO 89/01973) (ATCC VR-111; ATCC VR-2010); SV40 (Mulligan et al., Nature 277:108, 1979) (ATCC VR-305), (Madzak et al., J. Gen. Vir. 73:1533, 1992); influenza virus (Luytjes et al., Cell 59:1107,1989; McMicheal et al., The New England Journal of Medicine 309:13, 1983; and Yap et al., Nature 273:238, 1978) (ATCC VR-797); parvovirus such as adeno-associated virus (Samulski et al., J. Vir. 63:3822, 1989, and Mendelson et al., Virology 166:154,1988) (ATCC VR-645); herpes simplex virus (Kit et al., Adv. Exp. Med. Biol. 215:219, 1989) (ATCC VR-977; ATCC VR-260); Nature 277:108, 1979); human immunodeficiency virus (EPO 386, 882, Buchschacher et al., J. Vir. 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

A CIF150/hTAF$_{II}$150 polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

In an alternative embodiment, a CIF150/hTAF$_{II}$150 polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry*, pp. 236–240, 1975 (W. H. Freeman, San Francisco, Calif.); Szoka et al., *Biochim. Biophys. Acta* 600:1, 1980; Bayer et al., *Biochim. Biophys. Acta.* 550:464, 1979; Rivnay et al., *Meth. Enzymol.* 149:119, 1987; Wang et al., *Proc. Natl. Acad. Sci. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising CIF150/hTAF$_{II}$150 polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84:7413–7416, 1987), mRNA (Malone et al., *Proc. Natl. Acad. Sci. USA* 86:6077–6081, 1989), and purified transcription factors (Debs et al., *J. Biol. Chem.* 265:10189–10192, 1990), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Felgner et al., *Proc. Natl. Acad. Sci. USA* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* 75:4194–4198, 1978; and WO 90/11092 for descriptions of the synthesis of DOTAP (1,2-bis(oleoyloxy)-3-(trimethylammonio)propane)liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512–527; Szoka et al., *Proc. Natl. Acad. Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Natl. Acad. Sci. USA* 76:3348, 1979; Enoch and Strittmatter, *Proc. Natl. Acad. Sci. USA* 76:145, 1979; Fraley et al., *J. Biol. Chem.* 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with a CIF150/hTAF$_{II}$150 polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked CIF150/hTAF$_{II}$150 polynucleotide molecules are used as gene delivery vehicles, as described in WO 90/11092 and U.S. Pat. No. 5,580,859. Such gene delivery vehicles can be either CIF150/hTAF$_{II}$150 DNA or RNA and, in certain embodiments, are linked to killed adenovirus. Curiel et al., *Hum. Gene. Ther.* 3:147–154, 1992. Other suitable vehicles include DNA-ligand (Wu el al., *J. Biol. Chem.* 264:16985–16987, 1989), lipid-DNA combinations (Felgner et al., *Proc. Natl. Acad. Sci. USA* 84:7413 7417, 1989), liposomes (Wang et al., *Proc. Natl. Acad. Sci.* 84:7851–7855, 1987) and microprojectiles (Williams et al., *Proc. Natl. Acad. Sci.* 88:2726–2730, 1991).

One can increase the efficiency of naked CIF150/hTAF$_{II}$150 polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. CIF150/hTAF$_{II}$150 polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of CIF150/hTAF$_{II}$150 polynucleotides into the cytoplasm.

Expression of CIF150/hTAF$_{II}$150 protein and activity are cell cycle regulated. Thus, the invention provides compositions which can be used to alter spatial or temporal patterns of division of a human cell. Depletion of CIF150/hTAF$_{II}$150 activity leads to a $G_2$ (late S phase) arrest of the cell cycle, indicating that CIF150/hTAF$_{II}$150 function is required to transcribe genes necessary for cell cycle progression. Thus, mitosis or cell cycle progression can be reduced or prevented by decreasing expression of a human CIF150/hTAF$_{II}$150 gene. Decreased CIF150/hTAF$_{II}$150 gene expression can be used to treat conditions characterized by high rates of mitosis, such as neoplasia, metastasis of neoplasms, benign proliferative diseases, and dysplastic and hyperplastic disorders. Cells in which CIF150/hTAF$_{II}$150 expression has been decreased can also be used to identify genes whose expression is dependent on a CIF150/hTAF$_{II}$150 protein. Conversely, increased CIF150/hTAF$_{II}$150 expression can be used to expand cell populations in vitro or for treating disorders such as anemia, which are characterized by lowered rates of mitosis.

In one embodiment of the invention, expression of the CIF150/hTAF$_{II}$150 gene is decreased using a ribozyme, an RNA molecule with catalytic activity. See, e.g., Cech, 1987, *Science* 236:1532–1539; Cech, 1990, *Ann. Rev. Biochem.* 59:543–568; Cech, 1992, *Curr. Opin. Struct. Biol.* 2: 605–609; Couture and Stinchcomb, 1996, *Trends Genet.* 12: 510–515. Ribozymes can be used to inhibit gene function by cleaving an RNA sequence, as is known in the art (e.g., Haseloff et al., U.S. Pat. No. 5,641,673).

The coding sequence of the CIF150/hTAF$_{II}$150 gene can be used to generate ribozymes which will specifically bind to mRNA transcribed from a CIF150/hTAF$_{II}$150 gene. Methods of designing and constructing ribozymes which can cleave other RNA molecules in trans in a highly sequence specific manner have been developed and described in the art (see Haseloff et al., *Nature* 334:585–591, 1988). For example, the cleavage activity of ribozymes can be targeted to specific CIF150/hTAF$_{II}$150 RNAs by engineering a discrete "hybridization" region into the ribozyme. The hybridization region contains a sequence complementary to the target CIF150/hTAF$_{II}$150 RNA and thus specifically hybridizes with the target (see, for example, Gerlach et al., EP 321,201). The nucleotide sequence shown in SEQ ID NO:1 provides a source of suitable hybridization region sequences. Longer complementary sequences can be used to increase the affinity of the hybridization sequence for the target. The hybridizing and cleavage regions of the CIF150/hTAF$_{II}$150 ribozyme can be integrally related; thus, upon hybridizing to the target CIF150/hTAF$_{II}$150 RNA through the complementary regions, the catalytic region of the ribozyme can cleave the target.

CIF150/hTAF$_{II}$150 ribozymes can be introduced into cells, such as neoplastic cells, as part of a DNA construct, as is known in the art and described above. Mechanical methods, such as microinjection, liposome-mediated transfection, electroporation, or calcium phosphate precipitation, can be used to introduce the ribozyme-containing DNA construct into cells in which it is desired to decrease CIF150/hTAF$_{II}$150 expression. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of CIF150/hTAF$_{II}$150 ribozymes in the cells.

As taught in Haseloff et al., U.S. Pat. No. 5,641,673, CIF150/hTAF$_{II}$150 ribozymes can be engineered so that ribozyme expression will occur in response to factors which induce expression of the CIF150/hTAF$_{II}$150 gene. Ribozymes can also be engineered to provide an additional level of regulation, so that destruction of CIF150/hTAF$_{II}$150 mRNA occurs only when both a CIF150/hTAF$_{II}$150 ribozyme and a CIF150/hTAF$_{II}$150 gene are induced in the cells.

In another embodiment of the invention, expression of the CIF150/hTAF$_{II}$150 gene is altered using an antisense oligonucleotide sequence. The antisense sequence is complementary to at least a portion of the coding sequence of a CIF150/hTAF$_{II}$150 gene having the nucleotide sequence shown in SEQ ID NO:1. Preferably, the antisense oligonucleotide sequence is at least six nucleotides in length, but can be about 8, 12, 15, 20, 25, 30, 35, 40, 45, or 50 nucleotides long. Longer sequences can also be used. CIF150/hTAF$_{II}$150 antisense oligonucleotide molecules can be provided in a DNA construct and introduced into cells as described above, to decrease CIF150/hTAF$_{II}$150 expression.

Cells treated with an antisense oligonucleotide in order to interfere with expression of CIF150/hTAF$_{II}$150 arrest in the cell cycle in the S/G$_2$ phase. This result indicates that CIF150/hTAF$_{II}$150 function is important for cells to enter mitosis. The antisense oligonucleotide 5' TGCTCATGGA AGCATAAGCA GCCAC 3' (SEQ ID NO:5) reduces CIF150/hTAF$_{II}$150 mRNA levels in HeLa and IMR 90 cells (see Example 1). The treated cells do not enter mitosis and accumulate in G$_2$ phase. One of skill in the art can test other oligonucleotides for antisense effect, by delivering the antisense oligonucleotide to the cell using transfection or any means known in the art and detecting CIF150/hTAF$_{II}$150 mRNA levels.

CIF150/hTAF$_{II}$150 antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1–8; Sonveaux, 1994, *Meth. Mol. Biol.* 26:1–72; Uhlmann et al., 1990, *Chem. Rev.* 90:543–583.

Precise complementarity is not required for successful duplex formation between an antisense molecule and the complementary coding sequence of a CIF150/hTAF$_{II}$150 gene. Antisense molecules which comprise, for example, 2, 3, 4, or 5 or more stretches of contiguous nucleotides which are precisely complementary to a CIF150/hTAF$_{II}$150 coding sequence, each separated by a stretch of contiguous nucleotides which are not complementary to adjacent CIF150/hTAF$_{II}$150 coding sequences, can provide targeting specificity for CIF150/hTAF$_{II}$150 mRNA. Preferably, each stretch of contiguous nucleotides is at least 4, 5, 6, 7, or 8 or more nucleotides in length, Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular CIF130 coding sequence.

CIF150/hTAF$_{II}$150 antisense oligonucleotides can be modified without affecting their ability to hybridize to a CIF150/hTAF$_{II}$150 coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g, Agrawal et al., 1992, *Trends Biotechnol.* 10:152–158; Uhlmann et al., 1990, *Chem. Rev.* 90:543–584; Uhlmann et al., 1987, *Tetrahedron. Lett.* 215:3539–3542.

Antibodies which specifically bind to a CIF150/hTAF$_{II}$150 protein, particularly single-chain antibodies, can also be used to alter CIF150/hTAF$_{II}$150 gene expression. CIF150/hTAF$_{II}$150-specific antibodies bind to CIF150/hTAF$_{II}$150 protein and prevent the protein from functioning in the cell. Polynucleotides encoding antibodies which specifically bind to CIF150/hTAF$_{II}$150 can be introduced into cells as described above.

Preferably, the mechanism used to decrease expression of the CIF150/hTAF$_{II}$150 gene, whether ribozyme, antisense nucleotide sequence, or antibody, decreases expression of the CIF150/hTAF$_{II}$150 gene by 50%, 60%, 70%, or 80%. Most preferably, expression of the CIF150/hTAF$_{II}$150 gene is decreased by 90%, 95%, 99%, or 100%. The effectiveness of the mechanism chosen to alter expression of the CIF150/hTAF$_{II}$150 gene can be assessed using methods well known in the art, such as hybridization of nucleotide probes to CIF150/hTAF$_{II}$150 mRNA, quantitative RT-PCR, or detection of CIF150/hTAF$_{II}$150 protein using CIF150/hTAF$_{II}$150-specific antibodies.

Compositions comprising CIF150/hTAF$_{II}$150 antibodies, ribozymes, or antisense oligonucleotides can be used to treat proliferative disorders, such as neoplasias, dysplasias, and hyperplasias, and their symptoms. Neoplasias which can be treated with a CIF150/hTAF$_{II}$150 composition include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, and metastatic tumors. Proliferative disorders which can be treated with a CIF150/hTAF$_{II}$150 composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias, or pseudoepitheliomatous hyperplasia of the skin can be treated with CIF150/hTAF$_{II}$150 compositions.

Even in disorders in which CIF150/hTAF$_{II}$150 mutations are not implicated, decreasing CIF150/hTAF$_{II}$150 function can have therapeutic application. In these disorders, decreasing CIF150/hTAF$_{II}$150 expression or function can help to suppress tumors. Similarly, in tumors in which CIF150/hTAF$_{II}$150 expression is not aberrant, effecting CIF150/hTAF$_{II}$150 downregulation or decrease of CIF150/hTAF$_{II}$150 activity can suppress metastases.

CIF150/hTAF$_{II}$150 compositions of the invention can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in CIF150/hTAF$_{II}$150 compositions, for example, mineral salts such as hydrochlorides, hydrobromides, phosphates, or sulfates, as well as salts of organic acids such as acetates, proprionates, malonates, or benzoates. CIF150/hTAF$_{II}$150 compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a CIF150/hTAF$_{II}$150 composition.

Typically, a CIF150/hTAF$_{II}$150 composition is prepared as an injectable, either as a liquid solution or suspension; however, solid forms suitable for solution or suspension in liquid vehicles prior to injection can also be prepared. A CIF150/hTAF$_{II}$150 composition can also be formulated into an enteric coated tablet or gel capsule according to known methods in the art, such as those described in U.S. Pat. No. 4,853,230, EP 225,189, AU 9,224,296, and AU 9,230,801.

Administration of CIF150/hTAF$_{II}$150 compositions of the invention can include local or systemic administration, including injection, oral administration, particle gun, or catheterized administration, and topical administration. Various methods can be used to administer a CIF150/hTAF$_{II}$150 composition directly to a specific site in the body. For example, a small metastatic lesion can be located and an appropriate CIF150/hTAF$_{II}$150 composition injected several times in several different locations within the body of the lesion. Alternatively, arteries which serve a tumor can be identified, and a CIF150/hTAF$_{II}$150 composition can be injected into such an artery, in order to deliver the composition directly into the tumor.

A tumor which has a necrotic center can be aspirated, and a CIF150/hTAF$_{II}$150 composition can be injected directly into the now empty center of the tumor. A CIF150/hTAF$_{II}$150 composition can also be administered directly to the surface of a tumor, for example, by topical application of the composition. X-ray imaging can be used to assist in certain of these delivery methods. Combination therapeutic agents, including reagents which specifically bind to a wild-type human CIF150/hTAF$_{II}$150 gene or expression product, together with other therapeutic agents, can be administered simultaneously or sequentially.

CIF150/hTAF$_{II}$150 compositions can be delivered to specific tissues using receptor-mediated targeted delivery. Receptor-mediated DNA delivery techniques are described in, for example, Findeis et al. (1993), *Trends in Biotechnol.* 11, 202–05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Alternatively, a CIF150/hTAF$_{II}$150 composition can be introduced into human cells ex vivo, and the cells then replaced into the human. Cells can be removed from a variety of locations including, for example, from a selected tumor or from an affected organ. A CIF150/hTAF$_{II}$150 composition can be inserted into non-tumorigenic cells, such as dermal fibroblasts or peripheral blood leukocytes. If desired, particular fractions of cells, such as T cell subsets or stem cells, can also be specifically removed from the blood (see, for example, PCT WO 91/16116). The removed cells can then be contacted with a CIF150/hTAF$_{II}$150 composition utilizing any of the above-described techniques, followed by the return of the cells to the human.

In another embodiment of the invention, mitosis or cell cycle progression can be induced, increased, or promoted by increasing expression of a CIF150/hTAF$_{II}$150 gene. Increasing CIF150/hTAF$_{II}$150 gene expression is useful, for example, for increasing the number of cells in a cell population in vitro or for treating disorders characterized by lowered rates of mitosis or cell cycle progression, such as anemia.

A composition comprising all or a portion of a CIF150/hTAF$_{II}$150 gene or expression product can be introduced into a cell. The entire CIF150/hTAF$_{II}$150 coding sequence or protein can be introduced, as described above. Alternatively, a portion of a CIF150/hTAF$_{II}$150 protein which promotes mitosis or cell cycle progression can be identified and that portion or a nucleotide sequence encoding it can be introduced into the cell. Portions of a CIF150/hTAF$_{II}$150 protein which promote mitosis or cell cycle progression can be identified by introducing expression constructs which express different portions of the protein into cells and measuring alterations in the rate of mitosis or cell cycle progression. Rates of mitosis can be measured, for example, by detecting incorporation of labeled nucleotides, as is known in the art.

CIF150/hTAF$_{II}$150 compositions which contain CIF150/hTAF$_{II}$150 subgenomic polynucleotides preferably contain an expression construct comprising a promoter and a polynucleotide segment encoding at least six contiguous amino acids of a CIF150/hTAF$_{II}$150 protein or protein variant. Within the expression construct, the polynucleotide segment is located downstream from the promoter, and transcription of the polynucleotide segment initiates at the promoter. A more complete description of gene transfer vectors, especially retroviral vectors, is contained in U.S. Ser. No. 08/869,309, which is incorporated herein by reference.

Both the dose of a particular CIF150/hTAF$_{II}$150 composition and the means of administering the composition can be determined based on specific qualities of the therapeutic composition, the condition, age, and weight of the patient, the progression of the particular disease being treated, and other relevant factors. If the composition contains CIF150/hTAF$_{II}$150 proteins, polypeptides, or antibodies, effective dosages of the composition are in the range of about 5 μg to about 50 μg/kg of patient body weight, about 50 μg to about 5 mg/kg, about 100 μg to about 500 μg/kg of patient body weight, and about 200 to about 250 μg/kg.

Compositions containing CIF150/hTAF$_{II}$50 subgenomic polynucleotides, including antisense oligonucleotides and ribozyme- or antibody-encoding sequences, can be administered in a range of about 100 ng to about 200 mg of DNA for local administration. Suitable concentrations range from about 500 ng to about 50 mg, about 1 μg to about 2 mg, about 5 μg to about 500 μg, and about 20 μg to about 100 μg of DNA. Factors such as method of action and efficacy of transformation and expression are considerations which will affect the dosage required for ultimate efficacy of the CIF150/hTAF$_{II}$150 composition. If greater expression is desired over a larger area of tissue, larger amounts of CIF150/hTAF$_{II}$150 compositions or the same amount administered successively, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous CIF150/hTAF$_{II}$150 gene in a cell can be altered by introducing in frame with the endogenous CIF150/hTAF$_{II}$150 gene a DNA construct comprising a CIF150/hTAF$_{II}$150 targeting sequence, a regulatory sequence, an exon, and an unpaired splice donor site by homologous recombination, such that a homologously recombinant cell comprising a new CIF150/hTAF$_{II}$150 transcription unit. The new transcription unit can be used to turn the CIF150/hTAF$_{II}$150 gene on or off as desired. This method of affecting endogenous gene expression is taught in U.S. Pat. No. 5,641,670.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous CIF150/hTAF$_{II}$150 gene. The exogenous regulatory sequence directs transcription of the coding sequence of the CIF150/hTAF$_{II}$150 gene.

CIF150/hTAF$_{II}$150 and its binding element 5'-Py X G A G A/C A/Py -3' (SEQ ID NO:7) can be used to increase expression of a gene, either in vitro, such as in a cell culture, or in vivo. The CIF150/hTAF$_{II}$150 binding element can be inserted into the promoter region of a gene whose increased expression is desired. The promoter region is preferably a TATA-less promoter region. Any gene of interest can be placed under control of a TATA-less promoter region comprising a CIF150/hTAF$_{II}$150 binding element using standard recombinant DNA techniques.

The promoter region of the gene is contacted with a CIF150/hTAF$_{II}$150 protein The CIF150/hTAF$_{II}$150 protein can be provided to the promoter region, for example, by means of an expression construct which encodes CIF150/hTAF$_{II}$150. Upon binding of CIF150/hTAF$_{II}$150 to the CIF150/hTAF$_{II}$150 binding element of the promoter region, expression of the desired gene is increased The CIF150/hTAF$_{II}$150 coding sequence can be placed under control of a cell-type specific or inducible promoter, as is known in the art.

The present invention also provides a method of diagnosing or prognosing neoplasia or of identifying neoplastic tissue of a human. Expression of a human CIF150/hTAF$_{II}$150 gene can be compared between a first tissue which is suspected of being neoplastic and a second tissue which is normal. The first and second tissues can be obtained from the same human or from different humans. The normal tissue can be any tissue of the human, including, but not limited to, spleen, thymus, prostate, testis, ovary, small intestine, mucosal lining of the colon, peripheral blood leukocytes, heart, glial cells, placenta, lung, liver, skeletal muscle, kidney, pancreas, peripheral blood leukocytes, bone marrow, and appendix. The tissue suspected of being neoplastic can be derived from a different tissue type of the human, but preferably it is derived from the same tissue type, for example an intestinal polyp or other abnormal growth.

Overexpression of the CIF150/hTAF$_{II}$150 gene in the suspect tissue identifies the suspect tissue as neoplastic. Expression of a CIF150/hTAF$_{II}$150 gene can be detected by measuring CIF150/hTAF$_{II}$150 mRNA. PolyA$^+$ RNA can be isolated from the two tissues as is known in the art. One of skill in the art can readily determine differences in the size or amount of CIF150/hTAF$_{II}$150 mRNA transcripts between the two tissues that are compared, using Northern blots or in situ hybridization with nucleotide probes selected from the nucleotide sequence shown in SEQ ID NO:1. Overexpression of CIF150/hTAF$_{II}$150 mRNA in a tissue sample suspected of being neoplastic compared with the expression of CIF150/hTAF$_{II}$150 mRNA in a normal tissue is indicative of neoplasia.

Alternatively, CIF150/hTAF$_{II}$150 proteins can be compared between the two tissue samples. Any method for analyzing proteins can be used to compare two CIF150/hTAF$_{II}$150 proteins from matched samples. The sizes of the CIF150/hTAF$_{II}$150 proteins in the two tissues can be compared, for example, using antibodies to detect CIF150/hTAF$_{II}$150 proteins in Western blots of protein extracts from the two tissues. Other changes, such as expression levels and subcellular localization, can also be detected immunologically. A higher CIF150/hTAF$_{II}$150 protein expression level in a tissue suspected of being neoplastic compared with the CIF150/hTAF$_{II}$150 protein expression level in a normal tissue is indicative of neoplasia.

Similarly, comparison of CIF150/hTAF$_{II}$150 gene sequences or of CIF150/hTAF$_{II}$150 gene expression products, e.g., mRNA and protein, between a tissue of a human which is suspected of being neoplastic and a normal tissue of a human can be used to diagnose or prognose neoplasia in the human. The CIF150/hTAF$_{II}$150 genes in the two tissues can be compared by any means known in the art. For example, the two genes can be sequenced, and the sequence of the CIF150/hTAF$_{II}$150 gene in the tissue suspected of being neoplastic can be compared with the wild-type CIF150/hTAF$_{II}$150 sequence in the normal tissue. The CIF150/hTAF$_{II}$150 genes or portions of the CIF150/hTAF$_{II}$150 genes in the two tissues can be amplified, for example, using nucleotide primers selected from the nucleotide sequence shown in SEQ ID NO:1 in the polymerase chain reaction (PCR) or other amplification technique. The amplified genes or portions of genes can be hybridized to nucleotide probes selected from the nucleotide sequence shown in SEQ ID NO:1. The nucleotide probes can be labeled by a variety of methods, such as radiolabeling, biotinylation, or coupling to fluorescent or chemiluminescent tags, and detected by standard methods known in the art. Comparisons of CIF150/hTAF$_{II}$150 genes, mRNA, or protein can be made as described above.

A difference between the CIF150/hTAF$_{II}$150 genes (or a gene which regulates, for example, the expression, half-life, or degradation of CIF150/hTAF$_{II}$150 mRNA) in the two tissues which are compared indicates neoplasia in the suspect tissue. The degree of overexpression of the CIF150/hTAF$_{II}$150 gene in the neoplastic tissue relative to wild-type expression of the gene in normal tissue, or differences in the amount of overexpression of the CIF150/hTAF$_{II}$150 gene in the neoplastic tissue over time, can be used to prognose the progression of the neoplasia in that tissue or to monitor the response of the neoplastic tissue to various therapeutic regimens.

A genetic predisposition to neoplasia in a human can be detected by comparing a wild-type CIF150/hTAF$_{II}$150 gene, mRNA, or protein with a CIF150/hTAF$_{II}$150 gene, mRNA, or protein in a fetal tissue. Fetal tissues which can be used for this purpose include, but are not limited to, amniotic fluid, chorionic villi, blood, and the blastomere of an in vitro-fertilized embryo. The wild-type CIF150/hTAF$_{II}$150 gene can be obtained from any tissue. The mRNA or protein can be obtained from a normal tissue of a human in which the CIF150/hTAF$_{II}$150 gene is expressed. Such tissues are disclosed above. Differences, such as alterations in the nucleotide sequence or size of the fetal CIF150/hTAF$_{II}$150 gene or mRNA, or alterations in the molecular weight, amino acid sequence, or relative abundance of fetal CIF150/hTAF$_{II}$150 protein, indicate a germline mutation in the CIF150/hTAF$_{II}$150 gene of the fetus which indicates a genetic predisposition to neoplasia.

Kits for use in the diagnostic methods described above are also provided. CIF150/hTAF$_{II}$150 diagnostic kits comprise reagents which specifically bind to a human CIF150/hTAF$_{II}$150 gene or expression product and which can be used in methods of the invention, such as CIF150/hTAF$_{II}$150 subgenomic polynucleotide probes or antibodies. Means for labeling the probes or antibodies, reagents for use in the methods, such as buffers, and instructions for using the kits can also be included.

The invention provides a means of identifying compounds which induce or prevent mitosis or cell cycle progression. A cell is contacted with a test compound. The test compound can be a pharmacologic agent already known in the art or can be a compound previously unknown to have any pharmacological activity. The test compound can be naturally occurring or designed in the laboratory. It can be isolated from microorganisms, animals, or plants, and can be produced recombinantly, or synthesized by chemical methods known in the art.

The cell can be any primary human cell or human cell line which expresses a CIF150/hTAF$_{II}$150 gene, as disclosed above. Methods of establishing cultures of primary human cells or of culturing cell lines are well known in the art.

Expression of the CIF150/hTAF$_{II}$150 gene is detected. Means of detecting CIF150/hTAF$_{II}$150 gene expression, by measuring CIF150/hTAF$_{II}$150 mRNA or CIF150/hTAF$_{II}$150 protein, are disclosed above. Expression can be measured in a sample of the same cell population before and after contact with the test compound. Alternatively, control cell populations can be employed. A test compound which increases expression of the CIF150/hTAF$_{II}$150 gene is identified as a potential drug for inducing mitosis or cell cycle progression. A test compound which decreases expression of the CIF150/hTAF$_{II}$150 gene is identified as a potential drug for decreasing mitosis or cell cycle progression.

The function of CIF150/hTAF$_{II}$150 as a transcription factor can be exploited to identify genes whose transcription is dependent on the presence of CIF150/hTAF$_{II}$150. In one population of a cell type, such as HeLa or NIH 3T3 cells, expression of a CIF150/hTAF$_{II}$150 gene is unaltered; in another population of the cell type, expression of a CIF150/hTAF$_{II}$150 gene is decreased. RNA can be isolated from the two populations by methods well known in the art. Isolated RNA from the two populations can be compared to identify genes which are differentially transcribed in the two populations.

Decreased CIF150/hTAF$_{II}$150 expression can be achieved, for example, using ribozymes, antisense oligonucleotide sequences, or antibodies, as described above. The effectiveness of the mechanism chosen to alter expression of the CIF150/hTAF$_{II}$150 gene can be assessed using methods well known in the art, such as hybridization of nucleotide probes to CIF150/hTAF$_{II}$150 mRNA or detection of CIF150/hTAF$_{II}$150 protein using specific antibodies.

Genes which are differentially transcribed in the two populations can be compared, for example, using differential display PCR. Differential display PCR can be carried out on the two populations of cells using methods well known in the art. See, e.g., Liang & Pardee, 1992, *Science* 257:967–71; Bauer et al., 1993, *Nucl. Acids. Res.* 21:4272–80; Bauer et al., 1994, *PCR Methods Appl.* 4:S97–108; and Liang et al., 1995, *Meth. Enz.* 254:304–21. Kits for performing differential display PCR are available, for example, from Display Systems Biotech.

Briefly, total RNA is isolated form the two populations of cells. The RNA is reverse transcribed to produce a eDNA population which represents an overlapping subset of the total expression profile of the cells in each population. Each subset cDNA population is amplified using PCR with an anchored primer and a group of arbitrary primers in the presence of radiolabeled dATP. Amplified products from the two populations of cells are separated by gel electrophoresis, and patterns of separated products are detected, as is known in the art.

Differences in the two patterns, such as the presence, absence, altered position within the gel, or amount of one or more cDNA species, indicates that the expression of one or more genes was altered in response to decreasing the expression of the CIF150/hTAF$_{II}$150 gene. Differentially displayed bands can be excised from the gel, reamplified, and identified by sequence analysis. Optionally, the sequences can be cloned before sequencing. Sequences of the differentially displayed bands can be compared with known sequences in databases to determine the identity of genes whose expression was altered in response to decreasing expression of CIF150/hTAF$_{II}$150.

The invention also provides means of identifying compounds which alter mitosis or cell cycle progression. A cell population is contacted with a test compound. A test compound can be a pharmacologic agent already known in the art or can be a compound previously unknown to have any pharmacological activity. A test compound can be naturally occurring or designed in the laboratory. It can be isolated from microorganisms, animals, or plants, and can be produced recombinantly, or synthesized by chemical methods known in the art.

The cell population can comprise any primary human cell or human cell line which expresses a CIF150/hTAF$_{II}$150 gene, as disclosed above. Methods of establishing cultures of primary human cells or of culturing cell lines are well known in the art.

Expression of the CIF150/hTAF$_{II}$150 gene in the cell population is detected. Means of detecting CIF150/hTAF$_{II}$150 gene expression, for example by measuring CIF150/hTAF$_{II}$150 mRNA or CIF150/hTAF$_{II}$150 protein, are disclosed above. Expression can be measured in a sample of the same cell population before and after contact with the test compound. Alternatively, control cell populations which have not been contacted with the test compound can be employed. A test compound which increases expression of the CIF150/hTAF$_{II}$150 gene is identified as a potential compound for inducing mitosis or cell cycle progression. A test compound which decreases expression of the CIF150/hTAF$_{II}$150 gene is identified as a potential compound for inhibiting mitosis or cell cycle progression.

The invention also provides methods for screening test compounds for the ability to interfere with the binding of CIF130 to CIF150/hTAF$_{II}$150. According to one method, at least a CIF150/hTAF$_{II}$150-binding domain of a CIF130 protein as shown in SEQ ID NO:2 and at least a CIF130-binding domain of a CIF150/hTAF$_{II}$150 protein as shown in SEQ ID NO:4 are incubated together in the presence of a test compound. A full-length CIF130 and/or a CIF150/hTAF$_{II}$150 protein can also be used. In the absence of the test compound, the CIF150/hTAF$_{II}$150-binding domain binds to the CIF130-binding domain. The amount of bound and/or unbound proteins or binding domains is determined according to any technique known in the art, including any immunological technique. In order to facilitate the assay, one of the proteins or binding domains can be bound to a solid support, or can be labeled with a radiolabel, or other detectable label. A useful agent is identified which decreases the amount of a binding domain or a protein which is bound or increases the amount of a binding domain or a protein which is unbound. The binding domains or proteins can be prebound prior to the introduction of the test compound, or the test compound can be contacted with one of the two proteins or binding domains prior to incubation.

In another embodiment, a two-hybrid assay is used to screen compounds which inhibit the interaction between the binding partners, CIF130 and CIF150/hTAF$_{II}$150. According to such an assay, two fusion proteins, each comprising a binding domain of one of the binding partners, are used. The fusion proteins can comprise full-length CIF130 or CIF150/hTAF$_{II}$150 proteins or the portion of each protein necessary for the binding interaction. One of the binding partners is fused to a DNA binding domain and the other is fused to a transcriptional activating domain. If the fusion protein comprising the CIF150/hTAF$_{II}$150-binding domain comprises the DNA binding domain, then the fusion protein comprising the CIF130-binding domain comprises the transcriptional activating domain. If the fusion protein comprising the CIF130-binding domain comprises the DNA binding domain, then the fusion protein comprising the CIF150/hTAF$_{II}$150-binding domain comprises the transcriptional activating domain. The two fusion proteins interact to reconstitute a sequence-specific transcriptional activating factor. Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16.

The two fusion proteins are contained in a cell which also comprises a reporter gene. The reporter gene is sensitive to the activation of the reconstituted sequence-specific transcriptional activating factor. Suitable reporter genes whose expression can be conveniently detected include the E. coli lacZ gene, whose expression may be measured calorimetrically, and yeast selectable genes such as HIS3 or URA3.

The CIF150/hTAF$_{II}$150-binding domain of CIF130 and the CIF130-binding domain of CIF150/hTAF$_{II}$150 can be readily determined, for example, by testing various portions of each protein for the ability to bind to its partner. A variety of techniques can be used for this purpose, including but not limited to the yeast two-hybrid assay, affinity column chromatography, and polyacrylamide gel electrophoresis under non-reducing conditions.

In the absence of the test compound, the cell expresses the reporter gene. A test compound is added to the cell, and the effect on expression of the reporter gene is measured. A test compound which disrupts the binding of the CIF130 and CIF150/hTAF$_{II}$150 will have a negative effect on the transcriptional activation ability of the reconstituted sequence-specific transcriptional activating factor. Thus, expression of the reporter gene will be decreased. Compounds which decrease expression of the reporter gene are potential inducers of mitosis or cell cycle progression.

CIF150/hTAF$_{II}$150 subgenomic polynucleotides can also be delivered to subjects for the purpose of screening test compounds for those which are useful for enhancing transfer of CIF150/hTAF$_{II}$150 subgenomic polynucleotides to the cell or for enhancing subsequent biological effects of the CIF150/hTAF$_{II}$150 subgenomic polynucleotides within the cell. Such biological effects include hybridization to complementary CIF150/hTAF$_{II}$150 mRNA and inhibition of its translation, expression of the CIF150/hTAF$_{II}$150 subgenomic polynucleotide to form CIF150/hTAF$_{II}$150 mRNA and/or CIF150/hTAF$_{II}$150 protein, and replication and integration of the CFI50/hTAF$_{II}$150 subgenomic polynucleotide. Test compounds which can be screened include any substances, whether natural products or synthetic, which can be administered to the subject. Libraries or mixtures of compounds can be tested. The compounds or substances can be those for which a pharmaceutical effect is previously known or unknown. The compounds or substances can be delivered before, after, or concomitantly with the CIF150/hTAF$_{II}$150 subgenomic polynucleotides. They can be administered separately or in admixture with the CIF150/hTAF$_{II}$150 subgenomic polynucleotides.

Integration of delivered CIF150/hTAF$_{II}$150 subgenomic polynucleotides can be monitored by any means known in the art. For example, Southern blotting of the delivered CIF150/hTAF$_{II}$150 subgenomic polynucleotides can be performed. A change in the size of the fragments of the delivered polynucleotides indicates integration. Replication of the delivered polynucleotides can be monitored inter alia by detecting incorporation of labeled nucleotides combined with hybridization to a CIF150/hTAF$_{II}$150 probe. Expression of a CIF150/hTAF$_{II}$150 subgenomic polynucleotide can be monitored by detecting production of CIF150/hTAF$_{II}$150 mRNA which hybridizes to the delivered polynucleotide or by detecting CIF150/hTAF$_{II}$150 protein. CIF150/hTAF$_{II}$150 protein can be detected immunologically or by activity, for example by detecting binding to CIF130. Thus, delivery of CIF150/hTAF$_{II}$150 subgenomic polynucleotides according to the present invention provides an excellent system for screening test compounds for their ability to enhance delivery, integration, hybridization, expression, replication or integration in an animal, preferably a mammal, more preferably a human.

The complete consents of all references cited in this disclosure are incorporated herein by reference. The following are provided for exemplification purposes only and are not intended to limit the scope of the invention which has been described in broad terms above.

EXPERIMENTAL METHODS

Cell culture and cell-cycle analysis. IMR 90 (normal human lung fibroblasts) and HeLa cells were transfected with the phosphothiorate oligomers (100 to 400 nM) according to the manufacturer's protocol (Sequiur Inc.), using lipofection and OptiMEM (GibcoBRL). The transfected cells were harvested at various times post-lipofection for FACS and for Western and Northern analysis.

Initially, four single-strand antisense oligomers were designed to target distinct regions of CIF150/hTAF$_{II}$150 mRNA. The functional antisense oligomer designated B (5'-TGCTCATGGAAGCATAAGCAGCCAC-3'; SEQ ID NO:5) was used in combination with a control oligo Bx (5'-CACCGACGAATACGAAGGTACTCGT-3'; SEQ ID NO:6) containing the reverse sequence (3'-5') of the oligo B to assure identical nucleotide content. Density-arrested quiescent BALB/c3T3 and HeLa cells were prepared as previously described (Pledger et al., *Proc. Natl. Acad. Sci. U.S.A.* 75, 2839–43, 1978).

To monitor cell synchrony, $10^6$ cells from each sample were fixed in ethanol, treated with RNAase A (0.5 mg/ml, 1 hour at 37° C.), and stained with propidium iodide (40 μg/ml) 2 hr at 4° C., than analyzed by flow cytometry on a Becton Dickinson FACScan.

Immunoblot analysis were performed as described (Zawel & Reinberg, *Ann. Rev. Biochem.* 64, 533–61, 1995) using CIF150/hTAF$_{II}$150-specific polyclonal antiserum generated against the N-terminal peptide MNRKKGDKGFESPRP (amino acids 11–25 of SEQ ID NO:2) or monoclonal antibodies specific for cyclin A, B1, and E (Santa Cruz biotechnology, Inc). Differential display was performed as described by the manufacturer (Genomyx, Corp.).

Transfection and Reporter Assays. Cyclin A (−887 to +136) (28) and cyclin B1(−893 to +110) (Oliphant et al., *Mol. Cell. Biol.* 9, 2944–49, 1989) promoter fragments were generated by PCR using HeLa DNA and cloned into the promoterless pGL3 luciferase reporter vector (Promega). All PCR-amplified fragments were verified by DNA sequencing. Cotransfections were performed in HeLa cells using a pEVRF1 (Cogswell et al., *Mol. Cell. Biol.* 15, 2782–90, 1995) based CIF150/hTAF$_{II}$150 expression vector (pEVRF-CIF150/hTAF$_{II}$150) or a pEVRF1-Ob expression plasmid in combination with the indicated reporter constructs. Luciferase activity was determined according to the manufacturer's protocol (Promega) 36 hr after transfection.

Purification of proteins. HeLa nuclear extracts and CIF150/hTAF$_{II}$150 depleted nuclear extract were prepared as described previously (Zawel & Reinberg, 1995). CIF150/hTAF$_{II}$150 protein was purified from SF9 cells under native conditions using the bacculovirus expression system (pBlueBacHis2, Invitrogen). Whole cell extract from Bacculo-infected SF9 cells were prepared by sonication and applied to TALON™ metal affinity resin (Clontech) according to the manufacturer's protocol applying immidazole step elution. Recombinant CIF150/hTAF$_{II}$150 protein was tested for CIF150/hTAF$_{II}$150 activity as described previously (Zawell & Reinberg, 1995; Kaufmann et al., 1996) and analyzed by SDS-PAGE (8%), followed by silver staining.

In vitro transcription and in vitro DNA binding assays. In vitro transcription reactions were performed using the templates containing the G-less cassette as described before (Zawell & Reinberg, 1995 and references therein). Plasmid DNAs containing cyclin A, cyclin B1, CMV promoter fragments were cloned upstream of a 180 bp G-less cassette using a PCR protocol (Zawell & Reinberg, 1995; Kaufmann et al., 1996).

For the complementation assay, 8 μl of the CIF150/hTAF$_{II}$150 depleted nuclear extract (4 mg/ml) were preincubated for 30 min at 4° C. in the presence of DNA template with 1, 2 and 4 μl of recombinant CIF150/hTAF$_{II}$150 protein (see FIG. 3A; 10 μl loaded), followed by addition of rNTPs to yield the following final concentrations: 500 μM ATP, 500 μM CTP, 500 μM GTP and 30 μM [α-$^{32}$P]UTP. $^{32}$P-labeled RNA products were digested 15 min with RNAase H1, resolved on an 8% polyacrylamide-urea gel, and visualized by autoradiography. Electrophoretic mobility shift assays were performed using 3 and 6 μl CIF150/hTAF$_{II}$150 in 40 μl GL-buffer as previously described (Zawell & Reinberg, 1995) with the exception that the reaction mixture contained 50 ng dGdC oligomer as competitor. After 30 min incubation at 40° C. the binding mixtures were loaded on a 6% TBE (0.5×) polyacrylamide gel. Signals were quantitated by Phosphorimager analysis (BioRad, Inc.).

EXAMPLE 1

This example demonstrates that reduction in CIF150/hTAF$_{II}$150 mRNA or protein levels causes arrest of cells in $G_2$.

Four different CIF150/hTAF$_{II}$150 specific antisense phosphorothioate otigonucleotides were tested for their ability to modulate CIF150/hTAF$_{II}$150 function. One antisense oligonucleotide (oligomer B, 5'-TGCTCATGGA AGCAT-AAGCA GCCAC-3'; SEQ ID NO:5) led to a concentration-dependent increase in $G_2$/M cells when transfected into HeLa cells (FIG. 1A), whereas the other three oligomers had no effect on cell cycle progression.

Figure 1B:
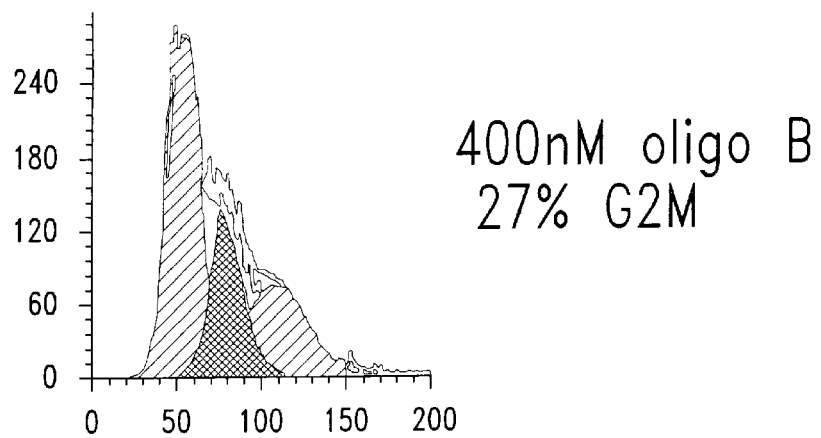
Figure 1B:
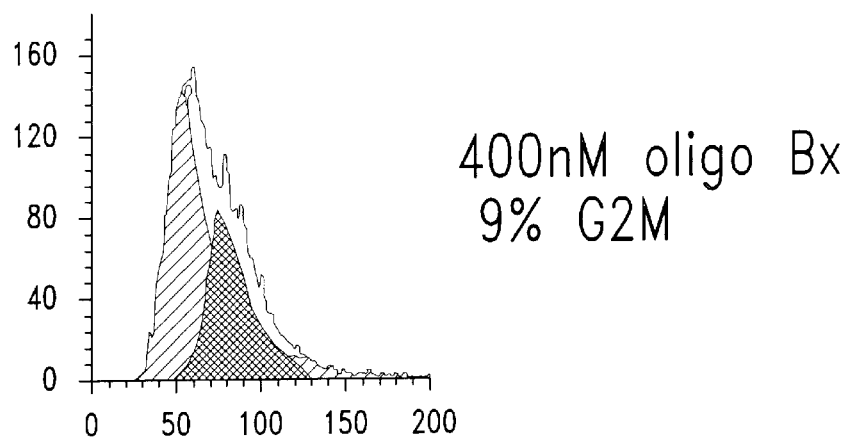
Figure 1B:
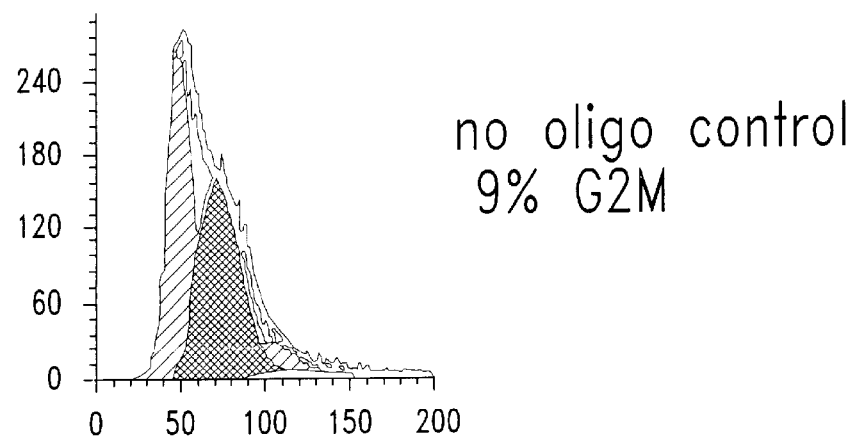
Figure 1C:
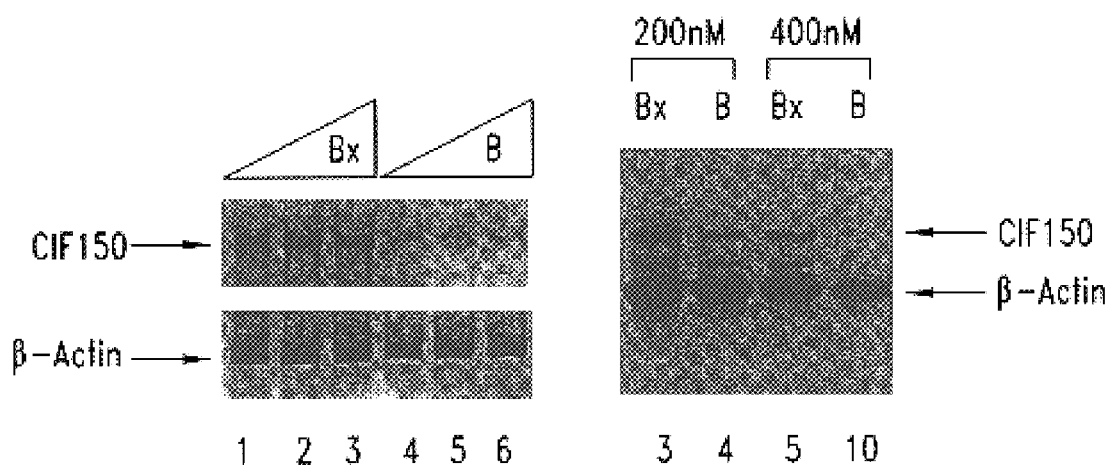

Because HeLa cells are highly transformed and bear defects in cell cycle checkpoints (p53$^-$- and RB$^-$), we confirmed the antisense effect using the primary lung fibroblast cell line IMR90 (FIG. 1B). A control oligo Bx (reverse sequence of B) did not affect the cell cycle progression in either cell line (FIGS. 1A and 1B). In FIG. 1C, we analyzed the RNA derived from HeLa cells treated with the antisense oligo B and the control oligo Bx. Quantitative RT-PCR (lanes 1 to 6) as well as Northern hybridization (lanes 7 to 10) revealed dramatically reduced CIF150/hTAF$_{II}$150 mRNA levels 24 h after antisense oligonucleotide treatment.

Figure 1D:
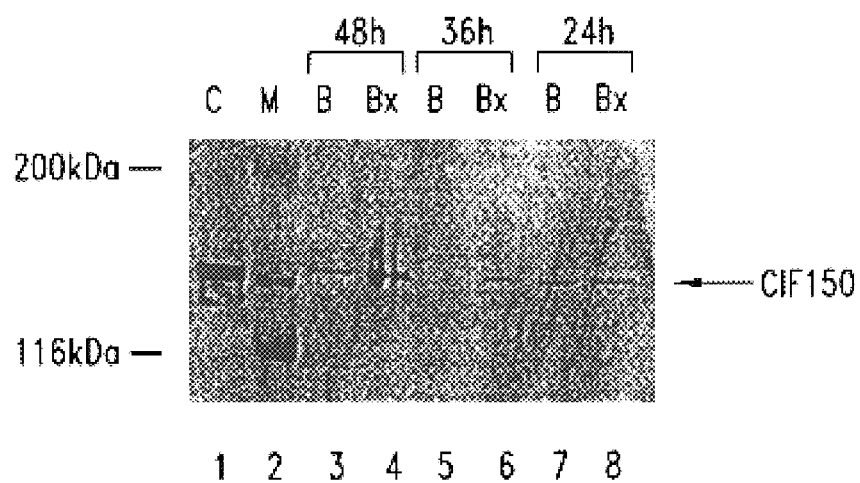
Figure 1E:
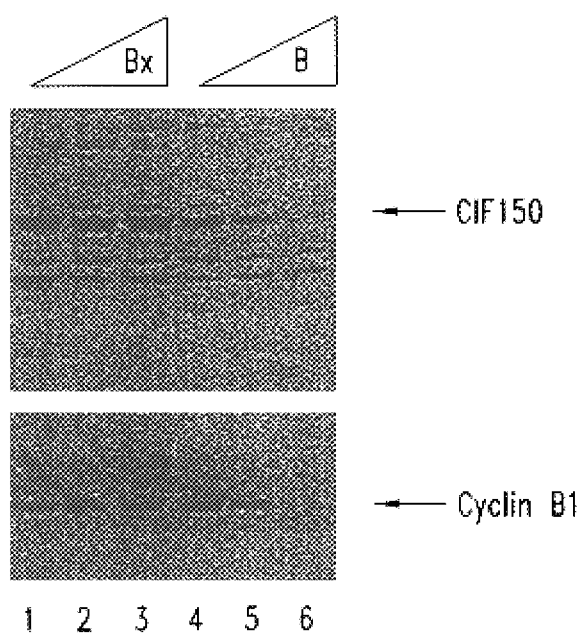

To demonstrate the antisense effect on CIF150/hTAF$_{II}$150 protein levels we performed an immunoblot analysis using CIF150/hTAF$_{II}$150-specific antiserum on cell lysates from different time points after antisense treatment (FIG. 1D and 1E). CIF150/hTAF$_{II}$150 protein decreased 36 h after antisense oligo treatment but remained unchanged after 24 h or in control oligonucleotide-treated cells (FIG. 1D). Since the cells were transiently transfected with the antisense oligomer, CIF150/hTAF$_{II}$150 protein level increased again after 48 h (lane 3). In order to confirm our FACS analysis, we analyzed cyclin B1 expression using extracts from antisense and control oligomer treated HeLa cells. Again, the level of CIF150/hTAF$_{II}$150 protein was reduced in a concentration-dependent manner using antisense oligo B (FIG. 1E, left panel). The level of cyclin B1 expression was similarly affected, indicating a cell cycle arrest and confirming our FACS analysis (FIG. 1E).

EXAMPLE 2

This example demonstrates that CIF150/hTAF$_{II}$150 mediates selective transcription of a specific set of genes.

To confirm our FACS analysis, we analyzed cyclin B1 expression using extracts from antisense and control oligomer treated HeLa cells. Again, CIF150/hTAF$_{II}$150 protein levels were concentration dependently reduced by using the antisense oligo B (FIG. 1E). The level of cyclin B1 expression seemed to be affected in the same way by the antisense treatment indicating a cell cycle arrest and confirming our FACS analysis (FIG. 1E).

Figure 1F:
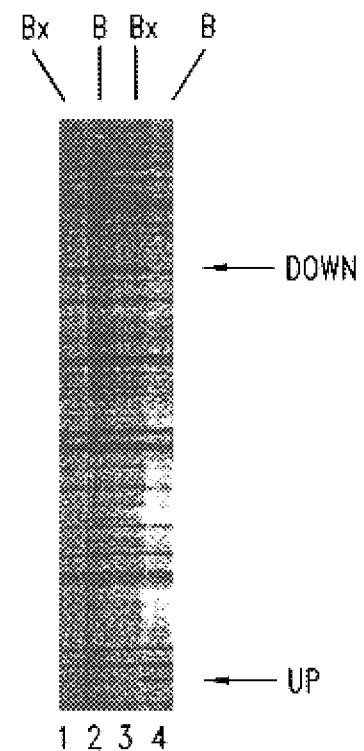

To address the question whether the decrease of cyclin B1 was a result of a more general effect on transcription in the absence of CIF150, we determined the expression levels of other mRNAs. We analyzed RNA derived from cells treated with the antisense or control oligonucleotides by differential PCR-display, in which each band is the PCR product of a specific mRNA. Only a minority of transcripts were affected by the loss of CIF150/hTAF$_{II}$150 function (FIG. 1F), suggesting that CIF150/hTAF$_{II}$150 mediates selective transcription of a specific set of class II genes. Similar results have been reported for a ts-mutant of mammalian TAF$_{II}$250 (Sekiguchi et al., *Gene Cells* 1, 687–705, 1996; Suzuki-Yagawa et al., *Mol. Cell. Biol.* 17, 3284–94, 1997; Ware et al., *Genes Dev.* 11, 2658–69 1977) and after functional knock-out experiments using yeast TAF$_{II}$90 (Apone et al., *Genes Dev.* 10, 2368–80, 1996) and TAF$_{II}$145 (Wieczorek et al., *Nature* 393, 187–91, 1998; Walker et al., *Cell* 90, 607–14, 1997; Sheu & Green, *Cell* 90, 615–24, 1997).

EXAMPLE 3

This example demonstrates that CIF150/hTAF$_{II}$150 expression and activity are cell cycle regulated and correlate with cyclin B1 and cyclin A transcription.

Figure 2A:
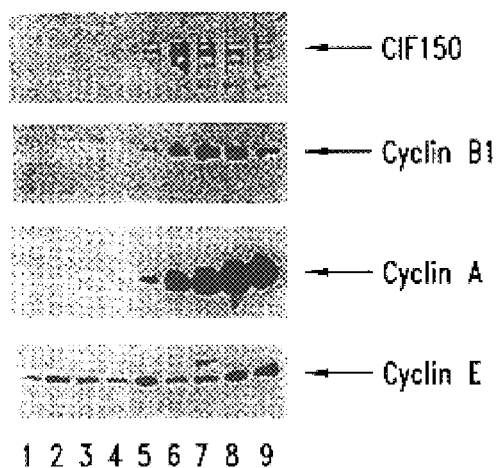
FIGS. 2A–2C. Regulation of CIF150/hTAF$_{II}$150 expression and activity is cell cycle dependent.
Figure 2B:
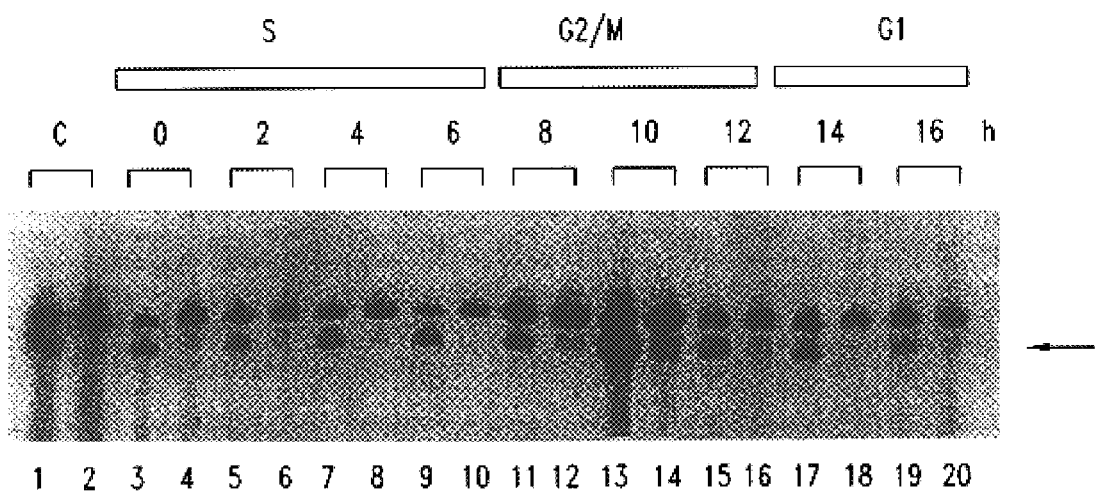

Serum-starved BALB/c 3T3 cells showed a lower level of CIF150/hTAF$_{II}$150 protein and an increase in CIF150/hTAF$_{II}$150 expression in G$_2$M after serum stimulation (FIG. 2A). CIF150/hTAF$_{II}$150 upregulation began approximately 15 hr after serum addition, just before Cyclin A and B1 expression (lanes 5 and 6). Cyclin E expression did not significantly change in this cell line and serves here as a loading control. We repeated the same experiments using HeLa cells and observed the same change in CIF150/hTAF$_{II}$150 and cyclin B1 expression (FIG. 2B).

Taken together, these results indicate that regulation of CIF150/hTAF$_{II}$150 protein levels is cell cycle dependent and suggests that CIF150/hTAF$_{II}$150 is a positive regulator of cyclin B1 and A expression.

EXAMPLE 4

This example demonstrates that CIF150/hTAF$_{II}$150 activity changes during cell cycle progression.

In vitro transcription assays were performed using HeLa nuclear extracts derived from different cell cycle stages after synchronization at the G$_1$/S boundary by a double thymidine block (Shen & Green, 1997; Rao & Johnson, *Nature* 225, 159–64, 1970; Lew et al., *Cell* 66, 1197–1206, 1991). CIF150/hTAF$_{II}$150activity was measured using synthetic Inr (TdT initiator)-containing and Inr-lacking promoters as described previously (Kaufmann et al., *Mol. Cell. Biol.* 18, 233–39, 1998). We observed an Inr-dependent increase in transcriptional activity in nuclear extracts derived from cells 8 to 12 hr after release from the double thymidine block (FIG. 2B; lanes 11, 13, and 15). This result clearly indicates a cell-cycle dependent change in CIF150/hTAF$_{II}$150 activity.

Figure 2C:
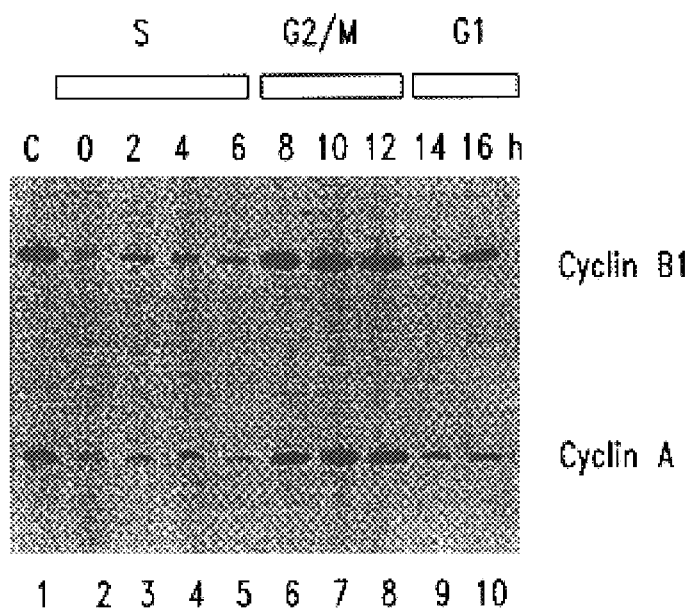

We then used the same nuclear extracts in combination with the TATA-less cyclin B1 and A promoter fragments fused to a G-less cassette in in vitro transcription assays (Zawell & Reinberg, 1995; Kaufmann et al., 1996). Both native promoters seemed to be more transcriptionally active only in the 8 to 12 hr nuclear extracts where CIF150/hTAF$_{II}$150 activity was strongest (FIG. 2C). In contrast, the activity of the TATA-box containing control promoters IgH and CMV did not correlate with CIF150/hTAF$_{II}$150 activity.

EXAMPLE 5

This example demonstrates that CIF150/hTAF$_{II}$150 is a positive regulator of cyclin B1 and A TATA-less promoters.

Figures 3A, 3B:
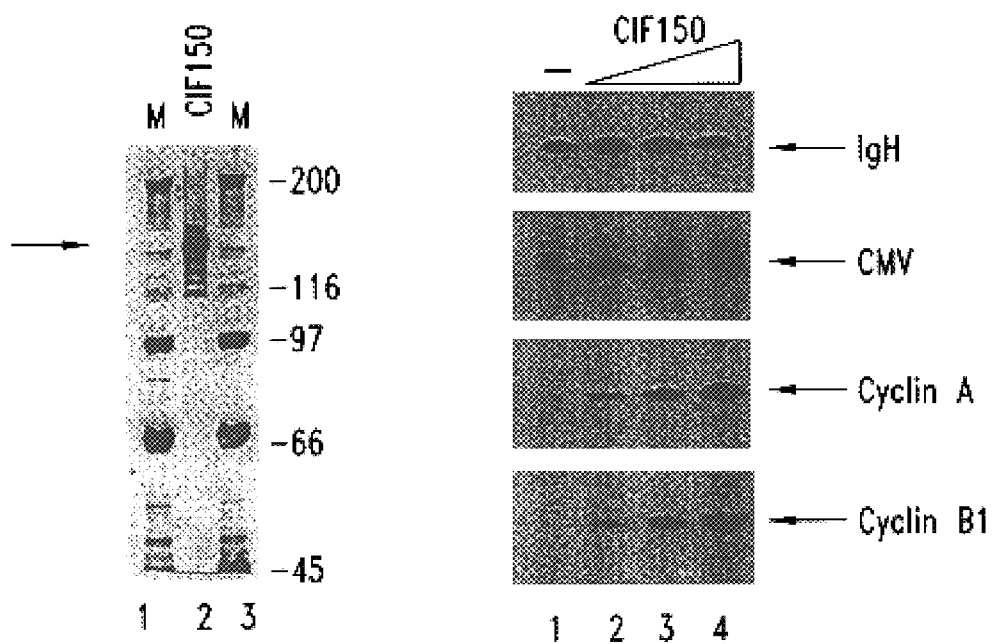
FIGS. 3A–3C. CIF150/hTAF$_{II}$150 is a positive regulator of cyclin B1 and cyclin A transcription.

To test whether CIF150/hTAF$_{II}$150 is a positive regulator of TATA-less promoters, we analyzed the effect of CIF150/hTAF$_{II}$150 in in vitro transcription and cotransfection assays. For in vitro transcription, we used highly purified recombinant CIF150/hTAF$_{II}$150 protein (FIG. 3A) in combination with nuclear extracts depleted for CIF150/hTAF$_{II}$150 activity, as described previously (Zawell & Reinberg, 1995). Cyclin B1 and A1 promoter-dependent transcription was not observed in the absence of CIF150/hTAF$_{II}$150 activity. Titration of CIF150/hTAF$_{II}$150 protein stimulated the TATA-less cyclin A and B1 promoters, indicating that CIF150/hTAF$_{II}$150 is required for their transcription (FIG. 3B, compare lane 1 with lanes 2, 3, and 4). The TATA-containing control promoters (IgH and CMV) were not affected by the absence of CIF150/hTAF$_{II}$150.

To demonstrate the stimulation affect of CIF150/hTAF$_{II}$150 in vivo, we performed cotransfection experiments of CIF150/hTAF$_{II}$150 expression vectors in combination with a luciferase reporter fused to cyclin B1 and A promoter fragments. Overexpression of CIF150/hTAF$_{II}$150 did have only a minor effect on the TATA-containing CMV and the minimal Fos promoter activity, but was able to stimulate cyclin B1 and cyclin A transcription in HeLa cells (FIG. 3C).

Figure 3C:
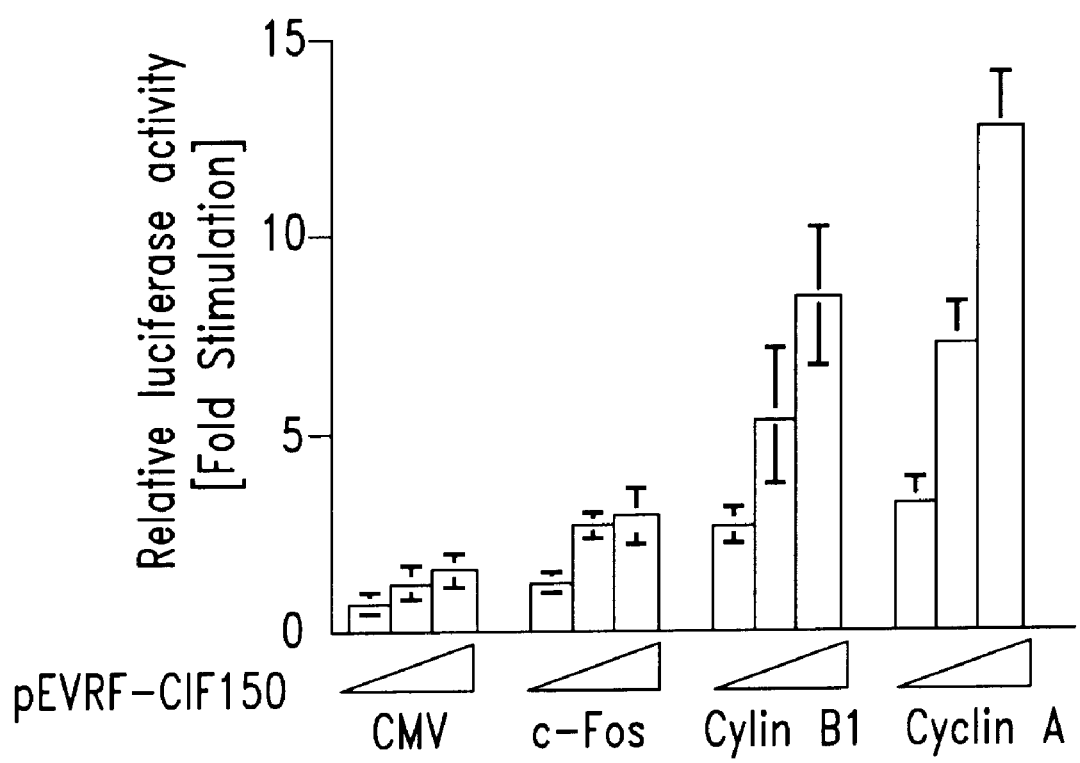

The upper panel of FIG. 3C shows absolute luciferase activities using the c-Fos, cyclin B1, and cyclin A promoters in cotransfection experiments with an unrelated expression plasmid (pEVRF1-Ob) and a CIF150/hTAF$_{II}$150 expression plasmid (pEVRF-CIF150). Both the cyclin A and B1 promoters are preferentially stimulated by CIF150/hTAF$_{II}$150 when compared to the TATA containing promoters c-Fos and CMV (see fold stimulation, lower panel of FIG. 3C).

These findings support our in vitro data suggesting that CIF150/hTAF$_{II}$150 is required for cyclin B1 and A transcription but is dispensable for transcription of TATA-containing promoters including the CMV, IgH, and the minimal Fos promoter.

EXAMPLE 6

This example demonstrates identification of a cis-acting CIF150/hTAF$_{II}$150 responsive element.

Because dTAF$_{II}$150 has been reported to recognize specific core promoter elements (Verrijzer et al., *Science* 264, 933–41, 1994) we have started to identify a cis-acting CIF150/hTAF$_{II}$150-responsive element. As a first step we performed bindingsite selection (Oliphant et al., 1989) using highly purified recombinant CIF150/hTAF$_{II}$150 (FIG. 3A). A pool of DNA fragments with 7 bp randomized nucleotide pairs were $^{32}$P-labeled and used in three successive rounds of gel shift experiments (FIG. 4A).

Figures 4A, 4B:
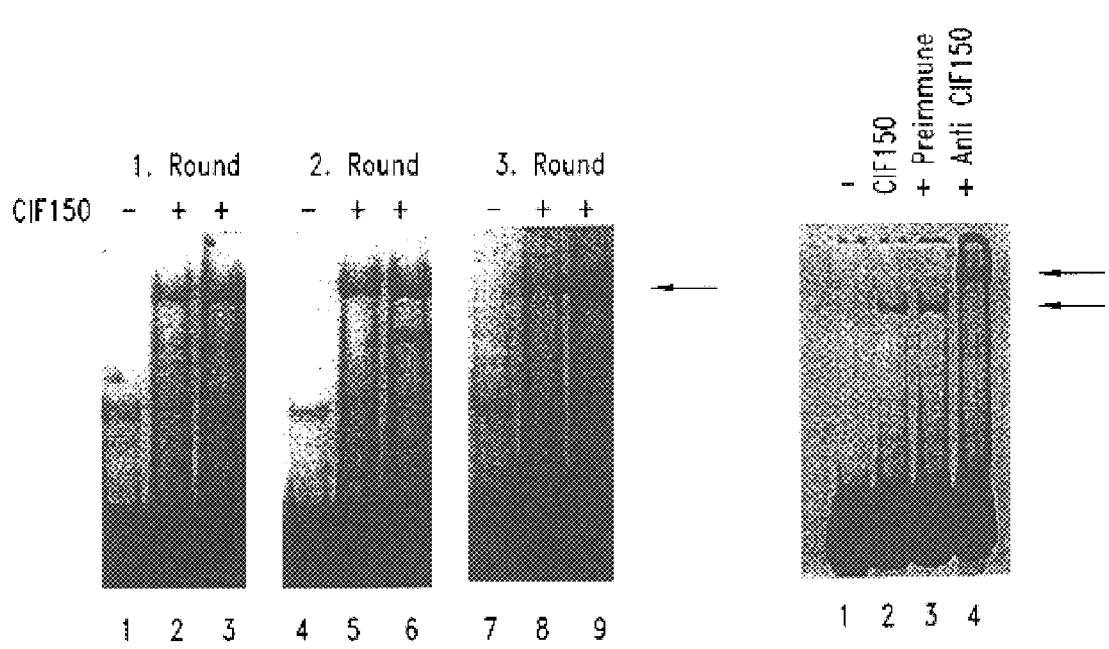

FIG. 4B shows that the selected protein-DNA complex is specific for CIF150/hTAF$_{II}$150 protein, as demonstrated by a supershift induced by CIF150/hTAF$_{II}$150-specific antiserum. DNA sequences of 44 selected PCR-fragments revealed a statistically significant enrichment of fragments with the core sequence 5'GAG3' (FIG. 2C). Affinity of CIF150/hTAF$_{II}$150 for the core sequence was improved only about five-fold after four rounds of selection (FIG. 4A), possibly due to the presence of cryptic binding sites in the flanking sequences of the PCR primers used (see FIG. 4B). Alternatively, CIF150/hTAF$_{II}$150 might be able to form stable complexes with non-specific DNA.

Figure 4D:
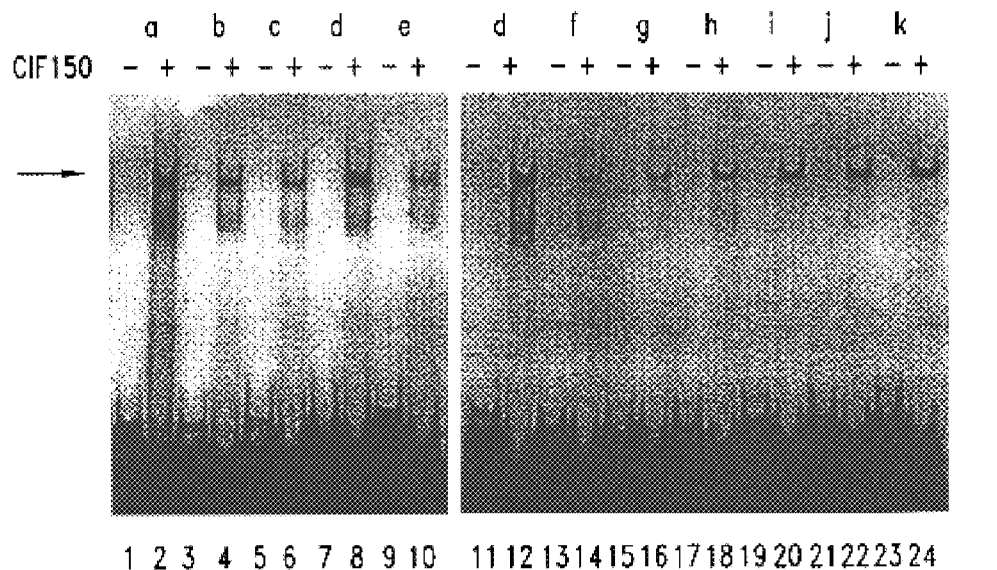

To validate further the putative sequence element, we performed electrophoretic mobility shift experiments using DNA fragments with defined base pair substitutions (FIG. 4D). Most substitutions reduced binding efficiency of CIF150/hTAF$_{II}$150 by 50%, with the exception of mutations which contain an intact GAG core sequence (FIG. 4D, compare oligo a and d with oligos b, c, e, f and g). These experiments clearly demonstrate that CIF150/hTAF$_{II}$150 binds the 5'GAG3' core sequence with higher affinity than randomized DNA (FIG. 4D; compare lane 11 with lanes 14, 16, and 18), indicating a potential role of CIF150/hTAF$_{II}$150 in promoter selection.

Figure 5:
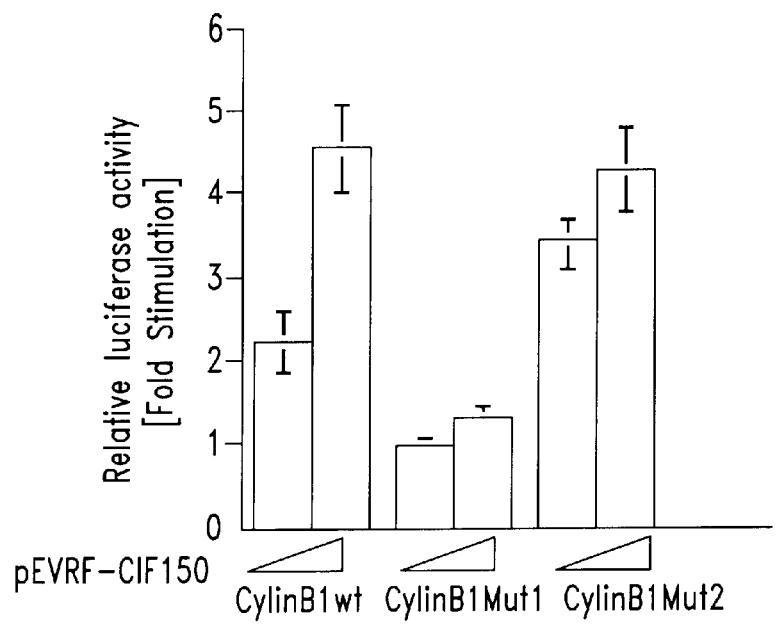
FIG. 5. Identification of a CIF150/hTAF$_{II}$150 binding element (CBE) in the cyclin B1 core promoter. Cotransfection of increasing amounts of CIF150/hTAF$_{II}$150 expression plasmid with cyclin B1 wild type and cyclin B1 promoter mutant. The values represent the average of three experiments.
Figure 5:

To test this idea we created point mutations in putative CIF150/hTAF$_{II}$150 binding elements (CBE) in the cyclin B1 core promoter and tested these constructs in cotransfection experiments (FIG. 5A). The substitution of the putative CIF150/hTAF$_{II}$150 binding site 5'-GAGGCTA-3' (SEQ ID NO:8) just 4 bp downstream of a non-canonical TATA box abolished the stimulation of reporter activity by CIF150/hTAF$_{II}$150 (FIG. 5).

These data suggest that CIF150/hTAF$_{II}$150 is a necessary positive transcriptional regulator of cell cycle progression through G$_2$/M. Furthermore, we provide additional evidence to support the idea that one of the regulatory functions of TAF$_{II}$s is to select core promoters. It is not known whether CIF150/hTAF$_{II}$150-dependent transcription of the TATA-less cyclin B1 and A promoters is still TBP-dependent. An attractive hypothesis is that CIF150/hTAF$_{II}$150 binding to the CBE element can compensate for the absence of TBP binding to the TATA-box.

What is claimed is:

1. An isolated and purified polynucleotide which encodes a protein comprising an amino acid sequence which is at least 85% identical to the amino acid sequence shown in SEQ ID NO:2.

2. The isolated and purified polynucleotide of claim 1 wherein the protein has the amino acid sequence shown in SEQ ID NO:2.

3. The isolated and purified polynucleotide of claim 2 which comprises the nucleotide sequence shown in SEQ ID NO:1.

4. An isolated and purified polynucleotide which comprises at least 11 contiguous nucleotides selected from the nucleotide sequence shown in SEQ ID NO:1.

5. A construct which comprises:
   a promoter; and
   a polynucleotide segment encoding a human CIF150/hTAF$_{II}$150 protein as shown in SEQ ID NO:2, wherein the polynucleotide segment is located downstream from the promoter, and wherein transcription of the polynucleotide segment initiates at the promoter.

6. An isolated host cell comprising a construct, wherein the construct comprises a promoter and polynucleotide segment encoding a human CIF150/hTAF$_{II}$150 protein as shown in SEQ ID NO:2.

7. A stably transformed isolated recombinant cell having incorporated therein a new transcription unit, wherein the new transcription unit comprises:
   (a) an exogenous regulatory sequence;
   (b) an exogenous exon, and
   (c) a splice donor site, wherein the transcription initiation unit is located upstream of a coding sequence of a CIF150/hTAF$_{II}$150 gene as shown in SEQ ID NO:1, wherein the exogenous regulatory sequence directs transcription of the coding sequence of the CIF150/hTAF$_{II}$150 gene.

8. A method to aid in the diagnosis or prognosis of neoplasia in a human, comprising the step of:
   comparing expression of a first CIF150/hTAF$_{II}$150 gene in a first tissue of a human suspected of being neoplastic with expression of a second CIF150/hTAF$_{II}$150 gene in a second tissue of a human which is normal, wherein the second CIF150/hTAF$_{II}$150 gene has the coding sequence shown in SEQ ID NO:1, wherein increased expression of the first CIF150/hTAF$_{II}$150 indicates neoplasia in the first tissue.

9. The method of claim 8 wherein CIF150/hTAF$_{II}$150 mRNAs in the first and second tissues are compared.

10. The method of claim 9 wherein CIF150/hTAF$_{II}$150 proteins in the first and second tissues are compared.

11. A method to aid in the diagnosis or prognosis of neoplasia in a human, comprising the step of:
   comparing a first human CIF150/hTAF$_{II}$150 gene, mRNA, or protein in a first tissue suspected of being neoplastic with a second human CIF150/hTAF$_{II}$150 gene, mRNA, or protein in a second tissue which is normal, wherein the second human CIF150/hTAF$_{II}$150 gene has the coding sequence shown in SEQ ID NO:1, wherein a difference between the first and second genes, mRNAs, or proteins indicates neoplasia in the first tissue.

12. The method of claim 11 wherein a CIF150/hTAF$_{II}$150 gene is compared.

13. The method of claim 11 wherein a CIF150/hTAF$_{II}$150 mRNA is compared.

14. The method of claim 11 wherein a CIF150/hTAF$_{II}$150 protein is compared.

15. The method of claim 11 wherein the first and second tissues are obtained from the same human.

16. A method to aid in detecting a genetic predisposition to neoplasia in a human, comprising:
   comparing a CIF150/hTAF$_{II}$150 gene, mRNA, or protein in a fetal tissue of a human with a wild-type human CIF150/hTAF$_{II}$150 gene, mRNA, or protein, wherein the wild-type human CIF150/hTAF$_{II}$150 gene has the coding sequence shown in SEQ ID NO:1, wherein a difference between the CIF150/hTAF$_{II}$150 gene, mRNA, or protein in the fetal tissue of the human and the wild-type human CIF150/hTAF$_{II}$150 gene, mRNA, or protein indicates a genetic predisposition to neoplasia in the human.

17. The method of claim 16 wherein a CIF150/hTAF$_{II}$150 mRNA is compared.

18. The method of claim 16 wherein a CIF150/hTAF$_{II}$150 gene is compared.

19. The method of claim 16 wherein a CIF150/hTAF$_{II}$150 protein is compared.

20. A method of screening test compounds for the ability to interfere with the binding of a CIF130 protein to a CIF150/hTAF$_{II}$150 protein, comprising the steps of:

(a) contacting a test compound with a CIF150/hTAF$_{II}$150-binding domain of a CIF130 protein as shown in SEQ ID NO:4 and a CIF130-binding domain of a CIF150/hTAF$_{II}$150 protein as shown in SEQ ID NO:2, wherein the CIF150/hTAF$_{II}$150-binding domain binds to the CIF130-binding domain in the absence of the test compound; and (b) determining the amount of CIF150/hTAF$_{II}$150-binding domains which are bound or unbound to CIF130-binding domains or determining the amount of CIF130-binding domains which are bound or unbound to CIF150/hTAF$_{II}$150-binding domains in the presence of the test compound, wherein a test compound which decreases the amount of bound CIF130- or CIF150/hTAF$_{II}$150-binding domains or which increases the amount of unbound CIF130- or CIF150/hTAF$_{II}$150-binding domains is a potential inducer of mitosis or cell cycle progression.

21. The method of claim 20 wherein the CIF130- and the CIF150/hTAF$_{II}$150-binding domains are prebound prior to the step of contacting.

22. The method of claim 20 wherein the test compound is contacted with either of the CIF130- or CIF150/hTAF$_{II}$150-binding domains prior to the step of contacting.

23. A method of screening test compounds for the ability to interfere with the binding of a CIF130 protein to a CIF150/hTAF$_{II}$150 protein, comprising the steps of:

(a) contacting a cell with a test compound, wherein the cell comprises:

i) a first fusion protein comprising (1) a CIF150/hTAF$_{II}$150-binding domain of a CIF130 protein as shown in SEQ ID NO:4 and (2) either a DNA binding domain or a transcriptional activating domain;

ii) a second fusion protein comprising a CIF130-binding domain of a CIF150/hTAF$_{II}$150 protein as shown in SEQ ID NO:2, wherein the CIF130-binding domain binds to the CIF150/hTAF$_{II}$150-binding domain, wherein if the first fusion protein comprises a DNA binding domain, then the second fusion protein comprises a transcriptional activating domain, wherein if the first fusion protein comprises a transcriptional activating domain, then the second fusion protein comprises a DNA binding domain, wherein the interaction of the first and second fusion proteins reconstitutes a sequence-specific transcription activating factor; and iii) a reporter gene comprising a DNA sequence to which the DNA binding domain specifically binds; and (b) measuring the expression of the reporter gene, wherein a test compound which decreases the expression of the reporter gene is a potential inducer of mitosis or cell cycle progression.

24. A method of increasing expression of a gene in an isolated cell, comprising the step of:

contacting a promoter region of a gene with a CIF150/hTAF$_{II}$150 protein as shown in SEQ ID NO:2, wherein the promoter region comprises a CIF150/hTAF$_{II}$150 binding element comprising a nucleotide sequence 5'-Py X G A G A/c A/Py-3' (SEQ ID NO:7), whereby expression of the gene is increased.

25. An antisense CIF150/hTAF$_{II}$150 oligonucleotide as shown in SEQ ID NO:5.

26. An isolated and purified polynucleotide which comprises 5'-Py X G A G A/c A/Py-3' (SEQ ID NO:7).

* * * * *

SEQUENCE LISTING

<160> NUMBER OF SEQ ID NOS: 6

<210> SEQ ID NO 1
<211> LENGTH: 3997
<212> TYPE: DNA
<213> ORGANISM: human

<400> SEQUENCE: 1

```
caagatgtcg gcggatggta gcttcgagcc cttgcggaga ggagcatctc tgtgacagaa      60
gcttgtcgac ggcggcttct aggagctagt cgaaggagcg aggttgaggc gggcagcgac     120
ccgtcaggtc gctcacctgg gcaccggcca gctgcgagac gtgacttggg gaccgcaggg     180
gagtggagag tgtgaggtgc caaagactag taatgccccg tatccccta ggaagccggg     240 aagccaagct ccgcgggacc gcttcatgcc gctgactggt gtagagcccg ccagaatgaa     300
caggaagaaa ggagacaagg gctttgaaag cccaaggcca tataaattaa cccatcaggt     360
cgtctgcatc aacaacataa atttccacag aaaatctgtt gtgggatttg tggaactgac     420
tatattcccc acagttgcaa acttgaatag aatcaagttg aacagcaaac agtgtagaat     480
ataccgagta aggatcaatg atttagaggc tgcttttatt tataatgacc caaccttgga     540
agtttgtcac agtgaatcaa aacagagaaa cctcaattat ttttccaatg cttatgcagc     600
tgcagttagt gctgtggacc ctgatgcagg aaatggagaa ctttgcatta aggttccatc     660
agagctatgg aaacacgttg atgagttaaa ggtcctgaag atacacatca attttctttt     720
ggatcagccc aaaggaggtc ttcattttgt ggtacccagt gtagagggaa gtatggcaga     780
gagaggtgct catgttttct cttgtgggta tcaaaattct acaagatttt ggttcccttg     840
```

-continued

| | |
|---|---|
| tgttgattca tactctgaat tgtgtacatg gaaattagaa tttacagtag atgctgcaat | 900 |
| ggttgctgtt tctaatggcg atttggtgga gacagtgtat actcatgata tgaggaagaa | 960 |
| aactttccat tatatgctta ccattcctac agcagcgtca aatatctcct tggccattgg | 1020 |
| accatttgaa atactggtag atccatacat gcatgaggtt actcattttt gtttgcccca | 1080 |
| acttcttcca ttgctgaaac ataccacatc ataccttcat gaagtctttg aattttatga | 1140 |
| agaaattctt acatgtcgtt acccatactc ctgtttttaag actgtcttca ttgatgaggc | 1200 |
| ttatgttgaa gtggctgctt atgcttccat gagcattttt agcacaaatc ttttacacag | 1260 |
| tgccatgatt atagatgaga cacctttgac tagaaggtgt ttagcccaat ccttggccca | 1320 |
| gcagttttttt ggttgtttca tatctagaat gtcttggtct gatgaatggg tgctgaaggg | 1380 |
| aatttcaggc tatatctatg gactttggat gaaaaaaact tttggtgtta atgagtaccg | 1440 |
| ccattggatt aaagaggagc tagacaaaat agtggcatat gaactaaaaa ctggtggggt | 1500 |
| tttactacat cccatatttg gtggaggaaa agagaaggat aatccggctt cccatctaca | 1560 |
| cttttcaata aagcatccac atacactgtc ctgggaatac tacactatgt ttcagtgtaa | 1620 |
| agcccacctt gtgatgagat tgattgaaaa taggatcagt atggaattta tgctacaagt | 1680 |
| tttcaataaa ctgctaagtc tggctagtac tgcttcatct cagaagttcc agtcacatat | 1740 |
| gtggagtcag atgttggttt ccacatctgg gttttttgaaa tccatttcaa atgtctctgg | 1800 |
| caaagatatt cagccgttaa taaagcagtg ggtagatcag agtggagtgg taaaatttta | 1860 |
| tggaagtttt gcatttaata gaaaacgaaa tgtcttggaa ctggaaataa aacaggacta | 1920 |
| tacatctcct ggaactcaga aatacgtggg accacttaaa gtgacagtgc aggagttaga | 1980 |
| tggatccttc aatcatacac tgcaaattga agaaaacagc cttaaacatg atataccctg | 2040 |
| ccattccaaa agtagaagga ataaaaagaa aaaatcccca ctgatgaatg gagaagaagt | 2100 |
| tgatatggat ctttctgcaa tggatgctga ttccccttttg ctgtggataa ggatagaccc | 2160 |
| agatatgtca gtattgagga aggtagaatt tgagcaagct gattttatgt ggcagtatca | 2220 |
| gctccgctat gagagagatg ttgttgcaca gcaggaatcc atttttggctt tggaaaaatt | 2280 |
| ccctactcca gcatctcggc ttgcactcac tgatatatta gaacaagagc agtgtttcta | 2340 |
| cagagtaaga atgtcagctt gtttctgtct tgcaaagatt gcaaattcaa tggtgagcac | 2400 |
| atggacagga ccaccagcca tgaagtcact cttcactagg atgttttgtt gtaaaagttg | 2460 |
| tccaaacatt gtgaaaacaa acaactttat gagctttcaa agctattttc tacagaagac | 2520 |
| tatgccagtt gcaatggctt tattaagaga tgttcataat cttttgtccta agaagtctt | 2580 |
| aacatttatt ttagacttaa tcaagtacaa tgacaacagg aaaaataagt tttcagataa | 2640 |
| ctattatcgt gcagaaatga ttgatgccct ggccaactct gttacacctg cagtcagtgt | 2700 |
| gaataatgaa gttagaactt tggataactt aaatcctgat gtgcgactca ttcttgaaga | 2760 |
| aatcaccaga ttttttgaata tggaaaaact tcttccgagt tacaggcata ccatcactgt | 2820 |
| cagttgtttg agagccatac gggtacttca gaagaacgga catgtgccaa gtgatccagc | 2880 |
| tcttttttaaa tcttatgctg aatatggcca cttttgtggac attaggatag cagctttgga | 2940 |
| agcagttgtt gattatacta aagtggacag aagttatgaa gaactgcaat ggctacttaa | 3000 |
| tatgattcag aatgaccctg taccctatgt aaggcataag attctcaaca tgttgactaa | 3060 |
| gaaccccccca tttactaaga acatggagtc tcccttatgc aatgaagccc tggtagatca | 3120 |
| actttggaaa cttatgaatt ctggtacttc acatgactgg aggttacggt gtggtgctgt | 3180 |
| ggacttgtac ttcacacttt ttggcctcag tagaccttcc tgtttaccct tgccagagct | 3240 |

```
tgggttggtt cttaatctaa aggagaaaaa agctgtcttg aatcctacca taattccaga    3300
gtcagtagca ggcaaccaag aagctgcaaa taatccaagc agtcacccac agctagttgg    3360
atttcagaac ccttttttcca gttctcaaga tgaggaggag attgatatgg atactgttca   3420
tgatagccag gccttcattt cccatcattt aaacatgctt gaaaggccgt caactccagg    3480
gctctcgaaa tatcggccag ctagctcccg atctgcttta ataccccagc actcagcagg    3540
ctgtgacagc acacccacca caaaacccca gtggagtttg aacttgcac ggaagggaac     3600 aggtaaagaa caagcacctt tggagatgag tatgcatcca gcggcaagcg ctccactctc    3660
agtctttact aaggaatcta cagcctccaa acacagtgac caccatcacc accatcacca    3720
tgagcacaag aaaaagaaga agaagcataa acataagcac aaacacaagc ataagcatga    3780
cagtaaagaa aaggacaagg agcctttcac tttctccagc cctgccagtg gcaggtctat    3840
tcgttctcct tccctttcag actgagaagg ggacaaaaag acctttcctt tcatgtccag    3900
aagaatgtat gtaactaaag ctttgtcctc tgtgaagaat tataaatgga gggggaaag     3960 gattcgcctc tcctacagaa attctgaatt catttaa                             3997
```

<210> SEQ ID NO 2
<211> LENGTH: 1199
<212> TYPE: PRT
<213> ORGANISM: human

<400> SEQUENCE: 2

```
Met Pro Leu Thr Gly Val Glu Pro Ala Arg Met Asn Arg Lys Lys Gly
  1               5                  10                  15

Asp Lys Gly Phe Glu Ser Pro Arg Pro Tyr Lys Leu Thr His Gln Val
             20                  25                  30

Val Cys Ile Asn Asn Ile Asn Phe His Arg Lys Ser Val Val Gly Phe
         35                  40                  45

Val Glu Leu Thr Ile Phe Pro Thr Val Ala Asn Leu Asn Arg Ile Lys
     50                  55                  60

Leu Asn Ser Lys Gln Cys Arg Ile Tyr Arg Val Arg Ile Asn Asp Leu
 65                  70                  75                  80

Glu Ala Ala Phe Ile Tyr Asn Asp Pro Thr Leu Glu Val Cys His Ser
                 85                  90                  95

Glu Ser Lys Gln Arg Asn Leu Asn Tyr Phe Ser Asn Ala Tyr Ala Ala
            100                 105                 110

Ala Val Ser Ala Val Asp Pro Asp Ala Gly Asn Gly Glu Leu Cys Ile
        115                 120                 125

Lys Val Pro Ser Glu Leu Trp Lys His Val Asp Glu Leu Lys Val Leu
    130                 135                 140

Lys Ile His Ile Asn Phe Ser Leu Asp Gln Pro Lys Gly Gly Leu His
145                 150                 155                 160

Phe Val Val Pro Ser Val Glu Gly Ser Met Ala Glu Arg Gly Ala His
                165                 170                 175

Val Phe Ser Cys Gly Tyr Gln Asn Ser Thr Arg Phe Trp Phe Pro Cys
            180                 185                 190

Val Asp Ser Tyr Ser Glu Leu Cys Thr Trp Lys Leu Glu Phe Thr Val
        195                 200                 205

Asp Ala Ala Met Val Ala Val Ser Asn Gly Asp Leu Val Glu Thr Val
    210                 215                 220

Tyr Thr His Asp Met Arg Lys Leu Thr Phe His Tyr Met Leu Thr Ile
225                 230                 235                 240
```

-continued

```
Pro Thr Ala Ala Ser Asn Ile Ser Leu Ala Ile Gly Pro Phe Glu Ile
            245                 250                 255

Leu Val Asp Pro Tyr Met His Glu Val Thr His Phe Cys Leu Pro Gln
        260                 265                 270

Leu Leu Pro Leu Leu Lys His Thr Thr Ser Tyr Leu His Glu Val Phe
    275                 280                 285

Glu Phe Tyr Glu Glu Ile Leu Thr Cys Arg Tyr Pro Tyr Ser Cys Phe
290                 295                 300

Lys Thr Val Phe Ile Asp Glu Ala Tyr Val Glu Val Ala Ala Tyr Ala
305                 310                 315                 320

Ser Met Ser Ile Phe Ser Thr Asn Leu Leu His Ser Ala Met Ile Ile
            325                 330                 335

Asp Glu Thr Pro Leu Thr Arg Arg Cys Leu Ala Gln Ser Leu Ala Gln
            340                 345                 350

Gln Phe Phe Gly Cys Phe Ile Ser Arg Met Ser Trp Ser Asp Glu Trp
        355                 360                 365

Val Leu Lys Gly Ile Ser Gly Tyr Ile Tyr Gly Leu Trp Met Lys Lys
    370                 375                 380

Thr Phe Gly Val Asn Glu Tyr Arg His Trp Ile Lys Glu Glu Leu Asp
385                 390                 395                 400

Lys Ile Val Ala Tyr Glu Leu Lys Thr Gly Gly Val Leu Leu His Pro
            405                 410                 415

Ile Phe Gly Gly Gly Lys Glu Lys Asp Asn Pro Ala Ser His Leu His
            420                 425                 430

Phe Ser Ile Lys His Pro His Thr Leu Ser Trp Glu Tyr Tyr Thr Met
        435                 440                 445

Phe Gln Cys Lys Ala His Leu Val Met Arg Leu Ile Glu Asn Arg Ile
    450                 455                 460

Ser Met Glu Phe Met Leu Gln Val Phe Asn Lys Leu Leu Ser Leu Ala
465                 470                 475                 480

Ser Thr Ala Ser Ser Gln Lys Phe Gln Ser His Met Trp Ser Gln Met
            485                 490                 495

Leu Val Ser Thr Ser Gly Phe Leu Lys Ser Ile Ser Asn Val Ser Gly
            500                 505                 510

Lys Asp Ile Gln Pro Leu Ile Lys Gln Trp Val Asp Gln Ser Gly Val
        515                 520                 525

Val Lys Phe Tyr Gly Ser Phe Ala Phe Asn Arg Lys Arg Asn Val Leu
    530                 535                 540

Glu Leu Glu Ile Lys Gln Asp Tyr Thr Ser Pro Gly Thr Gln Lys Tyr
545                 550                 555                 560

Val Gly Pro Leu Lys Val Thr Val Gln Glu Leu Asp Gly Ser Phe Asn
            565                 570                 575

His Thr Leu Gln Ile Glu Glu Asn Ser Leu Lys His Asp Ile Pro Cys
            580                 585                 590

His Ser Lys Ser Arg Arg Asn Lys Lys Lys Ile Pro Leu Met Asn
        595                 600                 605

Gly Glu Glu Val Asp Met Asp Leu Ser Ala Met Asp Ala Asp Ser Pro
    610                 615                 620

Leu Leu Trp Ile Arg Ile Asp Pro Asp Met Ser Val Leu Arg Lys Val
625                 630                 635                 640

Glu Phe Glu Gln Ala Asp Phe Met Trp Gln Tyr Gln Leu Arg Tyr Glu
            645                 650                 655
```

-continued

```
Arg Asp Val Val Ala Gln Gln Glu Ser Ile Leu Ala Leu Glu Lys Phe
            660                 665                 670

Pro Thr Pro Ala Ser Arg Leu Ala Leu Thr Asp Ile Leu Glu Gln Glu
            675                 680                 685

Gln Cys Phe Tyr Arg Val Arg Met Ser Ala Cys Phe Cys Leu Ala Lys
            690                 695                 700

Ile Ala Asn Ser Met Val Ser Thr Trp Thr Gly Pro Pro Ala Met Lys
705                 710                 715                 720

Ser Leu Phe Thr Arg Met Phe Cys Cys Lys Ser Cys Pro Asn Ile Val
                725                 730                 735

Lys Thr Asn Asn Phe Met Ser Phe Gln Ser Tyr Phe Leu Gln Lys Thr
            740                 745                 750

Met Pro Val Ala Met Ala Leu Leu Arg Asp Val His Asn Leu Cys Pro
            755                 760                 765

Lys Glu Val Leu Thr Phe Ile Leu Asp Leu Ile Lys Tyr Asn Asp Asn
            770                 775                 780

Arg Lys Asn Lys Phe Ser Asp Asn Tyr Tyr Arg Ala Glu Met Ile Asp
785                 790                 795                 800

Ala Leu Ala Asn Ser Val Thr Pro Ala Val Ser Val Asn Asn Glu Val
                805                 810                 815

Arg Thr Leu Asp Asn Leu Asn Pro Asp Val Arg Leu Ile Leu Glu Glu
            820                 825                 830

Ile Thr Arg Phe Leu Asn Met Glu Lys Leu Leu Pro Ser Tyr Arg His
            835                 840                 845

Thr Ile Thr Val Ser Cys Leu Arg Ala Ile Arg Val Leu Gln Lys Asn
            850                 855                 860

Gly His Val Pro Ser Asp Pro Ala Leu Phe Lys Ser Tyr Ala Glu Tyr
865                 870                 875                 880

Gly His Phe Val Asp Ile Arg Ile Ala Ala Leu Glu Ala Val Val Asp
                885                 890                 895

Tyr Thr Lys Val Asp Arg Ser Tyr Glu Glu Leu Gln Trp Leu Leu Asn
            900                 905                 910

Met Ile Gln Asn Asp Pro Val Pro Tyr Val Arg His Lys Ile Leu Asn
            915                 920                 925

Met Leu Thr Lys Asn Pro Pro Phe Thr Lys Asn Met Glu Ser Pro Leu
            930                 935                 940

Cys Asn Glu Ala Leu Val Asp Gln Leu Trp Lys Leu Met Asn Ser Gly
945                 950                 955                 960

Thr Ser His Asp Trp Arg Leu Arg Cys Gly Ala Val Asp Leu Tyr Phe
                965                 970                 975

Thr Leu Phe Gly Leu Ser Arg Pro Ser Cys Leu Pro Leu Pro Glu Leu
            980                 985                 990

Gly Leu Val Leu Asn Leu Lys Glu Lys Lys Ala Val Leu Asn Pro Thr
            995                 1000                1005

Ile Ile Pro Glu Ser Val Ala Gly Asn Gln Glu Ala Ala Asn Asn Pro
            1010                1015                1020

Ser Ser His Pro Gln Leu Val Gly Phe Gln Asn Pro Phe Ser Ser Ser
1025                1030                1035                1040

Gln Asp Glu Glu Glu Ile Asp Met Asp Thr Val His Asp Ser Gln Ala
                1045                1050                1055

Phe Ile Ser His His Leu Asn Met Leu Glu Arg Pro Ser Thr Pro Gly
            1060                1065                1070
```

```
Leu Ser Lys Tyr Arg Pro Ala Ser Ser Arg Ser Ala Leu Ile Pro Gln
        1075                1080                1085

His Ser Ala Gly Cys Asp Ser Thr Pro Thr Thr Lys Pro Gln Trp Ser
    1090                1095                1100

Leu Glu Leu Ala Arg Lys Gly Thr Gly Lys Glu Gln Ala Pro Leu Glu
1105                1110                1115                1120

Met Ser Met His Pro Ala Ala Ser Ala Pro Leu Ser Val Phe Thr Lys
                1125                1130                1135

Glu Ser Thr Ala Ser Lys His Ser Asp His His His His His His
            1140                1145                1150

Glu His Lys Lys Lys Lys Lys His Lys His Lys His Lys His Lys
        1155                1160                1165

His Lys His Asp Ser Lys Glu Lys Asp Lys Glu Pro Phe Thr Phe Ser
        1170                1175                1180

Ser Pro Ala Ser Gly Arg Ser Ile Arg Ser Pro Ser Leu Ser Asp
1185                1190                1195

<210> SEQ ID NO 3
<211> LENGTH: 3825
<212> TYPE: DNA
<213> ORGANISM: human

<400> SEQUENCE: 3 cgaaggggc ggagaggaag gagcgcggcg ggaccgggcc gggacagcgc gtactttggg      60
ctccgggatt cgctccgcgc ccgcggttgt agcagctgcc gctgcagcca tagcagcagg    120
tcagtcattg caccatgaa ctggaataaa ggtggtcctg cactaagcg aggatttggc      180 tttggaggtt ttgccatcag tgctgggaaa aggaggaac ccaaactccc acagcagtcc    240
cacagtgcct tggggcaac cagctcttct tctggatttg gaaagtcagc tccgccacag    300
cttccttctt tctacaaaat tggatctaag cgggccaact ttgatgaaga aaatgcctat   360
tttgaagatg aggaagaaga ttctagcaac gttgatttac cttacattcc tgctgaaaac   420
tcaccaactc gccaacaatt ccattccaag ccagtagatt ctgacagcga tgatgatccc   480
ttggaggcat tcatggctga ggtggaggat caggcggcta gagacatgaa gaggcttgaa   540
gaaaaggaca aggaaagaaa aaacgtaaag ggtattcgag atgacattga agaggaagat   600
gaccaagaag cttattttcg atacatggca gaaaacccaa ctgctggtgt ggttcaggag   660
gaagaggaag acaatctaga aatgatagt gacggaaatc caattgcacc taccaaaaaa   720
atcattgatc ctcttccccc cattgatcat tcagagattg actatccacc atttgaaaaa   780 aactttttaca atgagcatga agagataacc aacctcactc cacagcagtt aatagatctc   840
cggcataagc tcaatcttcg ggtctctggt gctgcacctc ctagaccagg aagtagcttt   900
gctcattttg ggtttgacga caacttatg caccagattc ggaaatctga atacacacag   960
cccactccaa tacagtgcca gggtgtgcct gtggcattaa gtggtagaga catgattggt  1020
attgccaaaa caggtagtgg gaaaactgca gccttcattt ggcccatgtt gattcatata  1080
atggaccaga aggagttgga accaggtgat ggaccaattg cagtgattgt gtgtcctacc  1140
agggagcttt gccagcagat ccatccagaa tgtaagcggt ttggaaaagc atataatctt  1200
cgatcagtgg ccgtatatgg aggagggagt atgtgggagc aggccaaggc ccttcaggag  1260
ggggcagaga ttgttgtgtg tacccccagt cgactgatag atcatgtgaa aaagaaagct  1320
accaatcttc aaagagtctc ttaccttgtg tttgatgaag cagatcgaat gtttgacatg  1380
ggatttgagt accagttcg atccatagca agtcatgttc gtcctgacag gcagactctc  1440
```

-continued

```
ttatttagtg caacttttcg gaagaagatt gaaaagttgg ccagagacat cctgatcgac      1500
cctattcgag tggtgcaggg agatattgga gaggcaaatg aagatgtgac acagattgtg      1560
gagattctcc attctggacc tagtaaatgg aactggctta cccggcgtct ggtagaattt      1620
acctcttcag ggagtgtcct cctctttgtt actaaaaaag ccaatgctga agagctagcg      1680
aataaccttt aacaggaggg tcataatctt gggctgctcc atgggatat ggatcagagt       1740
gagagaaaca aggtcatttc agactttaag aaaaaggaca tcccagtcct ggtggccaca      1800
gatgttgcag cccgtggtct ggacattcct tcaattaaga ctgtcattaa ctatgatgtg      1860
gcacgggaca ttgatacgca cactcacagg attggccgca caggaagagc gggtgagaaa      1920
ggtgtggcct atacctact cactcccaag gacagcaatt ttgctggtga cctggtccgg       1980
aacttggaag gagccaatca acacgtttct aaggaactcc tagatctggc aatgcagaat      2040
gcctggtttc ggaaatctcg attcaaagga gggaaaggaa aaaagctgaa cattggtgga      2100
ggaggcctag gctacaggga gcggcctggc ctgggctctg agaacatgga tcgaggaaat      2160
aacaatgtaa tgagcaatta tgaggcctac aagccttcca caggagctat gggagatcga      2220
ctaacggcaa tgaaagcagc tttccagtca cagtacaaga gtcactttgt tgcagccagt      2280
ttaagtaatc agaaggctgg aagttctgct gccggggcaa gtgggtggac tagtgcaggg      2340
agcttgaatt ctgttccaac taactcagca caacaggggcc ataacagtcc tgacagcccc    2400
gtcaccagtg ccgccaaggg catcccaggc tttggcaata ctggcaacat cagtggtgcc      2460
cctgtgacct acccgtctgc cggagcccaa ggagtcaaca acacagcttc agggaataac      2520
agccgagaag ggactggggg cagcaacggg aaaagggaga gatatactga gaaccggggc      2580
agcagccgtc acagtcacgg agagactggc aatcggcata cgatagtcc acgtcacgga      2640
gatggtggtc gccatggaga tggataccgc catccagaaa gcagcagccg tcatactgat      2700
ggccatcggc acgggagaa cagacatgga ggaagcgcag gccggcatgg ggagaaccgg       2760
ggtgcaaatg atggtcggaa tggggaaagc aggaaagaag cttttaatcg tgagggcaag     2820
atggagccca agatggaacc caagcgggac agcagcaaga tggacaaggt ggacagcaag     2880
acagataaga cagctgacgg ttttgctgtc ccagagccgc ctaaacgcaa gaaaggtcga     2940
tgggacagtt agaggggatg tgctaaagcg tgaaatcagt tgtccttaat ttttagaaag     3000
attttggtaa ctaggtgtct cagggctggg ttggggtcca aagtgtaagg accccctgcc     3060
cttagtggaa agctggagct tggagacatt accccttcat cagaaggaat tttcggatgt     3120
tttcttggga agctgttttg gtccttggaa gcagtgagag ctgggaagct tcttttggct     3180
ctaggtgagt tgtcatgcgg gtaagttgag gttatcttgg gataaagggt cttcagggc      3240
acaaaactca ctctaggttt atattatatg tagcttatat tttttactaa ggtgtcacct     3300
tataagcatc tataaattga gttctttttc ttagttgtat ggccaggcag tccccatttt     3360
aggagttggc ttctgcaaat tcaatccatt gagctaactg ttggggagca atttggtagt     3420
tgtagacatt tgcagggaag ggagatgtct gattctaaat gggagttgat gctcaggtcc     3480
ccagccaggt ttgcatccag ccctgagaca tgtaggaaac acctttcaga cccaggctct    3540
gaagattccc agaagccaca aggattgaag ggaaaaggtg atcctggtaa ctgttccagg    3600
attgctccag gtttgagatg gtattgctaa atttaaaatt aaacaagaga cccaacaaca    3660
gcttttaaag tgtcttctat ttcattgtat ttttttttaac ttgccccaat gatagaaaag   3720
tcttttgctg aaatgatttt gatgattttt gtttatcgtt tataaaaagg aaaagaaata   3780
taaaaaaaaa aaaaaaaaaa aaaaaaaaaa gcggccgctg aattc                    3825
```

-continued

```
<210> SEQ ID NO 4
<211> LENGTH: 1261
<212> TYPE: PRT
<213> ORGANISM: human

<400> SEQUENCE: 4

Arg Arg Gly Arg Arg Gly Arg Ser Ala Ala Gly Pro Gly Arg Asp Ser
 1               5                  10                  15

Ala Tyr Phe Gly Leu Arg Asp Ser Leu Arg Ala Arg Gly Cys Ser Ser
             20                  25                  30

Cys Arg Cys Ser His Ser Ser Arg Ser Val Ile Gly Thr Met Asn Trp
         35                  40                  45

Asn Lys Gly Gly Pro Gly Thr Lys Arg Gly Phe Gly Phe Gly Gly Phe
     50                  55                  60

Ala Ile Ser Ala Gly Lys Lys Glu Glu Pro Lys Leu Pro Gln Gln Ser
65                  70                  75                  80

His Ser Ala Phe Gly Ala Thr Ser Ser Ser Gly Phe Gly Lys Ser
             85                  90                  95

Ala Pro Pro Gln Leu Pro Ser Phe Tyr Lys Ile Gly Ser Lys Arg Ala
            100                 105                 110

Asn Phe Asp Glu Glu Asn Ala Tyr Phe Glu Asp Glu Glu Asp Ser
            115                 120                 125

Ser Asn Val Asp Leu Pro Tyr Ile Pro Ala Glu Asn Ser Pro Thr Arg
    130                 135                 140

Gln Gln Phe His Ser Lys Pro Val Asp Ser Asp Ser Asp Asp Pro
145                 150                 155                 160

Leu Glu Ala Phe Met Ala Glu Val Glu Asp Gln Ala Ala Arg Asp Met
                165                 170                 175

Lys Arg Leu Glu Glu Lys Asp Lys Glu Arg Lys Asn Val Lys Gly Ile
            180                 185                 190

Arg Asp Asp Ile Glu Glu Asp Gln Glu Ala Tyr Phe Arg Tyr
        195                 200                 205

Met Ala Glu Asn Pro Thr Ala Gly Val Val Gln Glu Glu Glu Asp
    210                 215                 220

Asn Leu Glu Tyr Asp Ser Asp Gly Asn Pro Ile Ala Pro Thr Lys Lys
225                 230                 235                 240

Ile Ile Asp Pro Leu Pro Ile Asp His Ser Glu Ile Asp Tyr Pro
                245                 250                 255

Pro Phe Glu Lys Asn Phe Tyr Asn Glu His Glu Ile Thr Asn Leu
            260                 265                 270

Thr Pro Gln Gln Leu Ile Asp Leu Arg His Lys Leu Asn Leu Arg Val
    275                 280                 285

Ser Gly Ala Ala Pro Pro Arg Pro Gly Ser Ser Phe Ala His Phe Gly
    290                 295                 300

Phe Asp Glu Gln Leu Met His Gln Ile Arg Lys Ser Glu Tyr Thr Gln
305                 310                 315                 320

Pro Thr Pro Ile Gln Cys Gln Gly Val Pro Val Ala Leu Ser Gly Arg
                325                 330                 335

Asp Met Ile Gly Ile Ala Lys Thr Gly Ser Gly Lys Thr Ala Ala Phe
            340                 345                 350

Ile Trp Pro Met Leu Ile His Ile Met Asp Gln Lys Glu Leu Glu Pro
        355                 360                 365

Gly Asp Gly Pro Ile Ala Val Ile Val Cys Pro Thr Arg Glu Leu Cys
    370                 375                 380
```

-continued

```
Gln Gln Ile His Pro Glu Cys Lys Arg Phe Gly Lys Ala Tyr Asn Leu
385                 390                 395                 400

Arg Ser Val Ala Val Tyr Gly Gly Ser Met Trp Glu Gln Ala Lys
            405                 410                 415

Ala Leu Gln Glu Gly Ala Glu Ile Val Val Cys Thr Pro Gly Arg Leu
            420                 425                 430

Ile Asp His Val Lys Lys Ala Thr Asn Leu Gln Arg Val Ser Tyr
            435                 440                 445

Leu Val Phe Asp Glu Ala Asp Arg Met Phe Asp Met Gly Phe Glu Tyr
450                 455                 460

Gln Val Arg Ser Ile Ala Ser His Val Arg Pro Asp Arg Gln Thr Leu
465                 470                 475                 480

Leu Phe Ser Ala Thr Phe Arg Lys Lys Ile Glu Lys Leu Ala Arg Asp
                485                 490                 495

Ile Leu Ile Asp Pro Ile Arg Val Val Gln Gly Asp Ile Gly Glu Ala
                500                 505                 510

Asn Glu Asp Val Thr Gln Ile Val Glu Ile Leu His Ser Gly Pro Ser
                515                 520                 525

Lys Trp Asn Trp Leu Thr Arg Arg Leu Val Glu Phe Thr Ser Ser Gly
530                 535                 540

Ser Val Leu Leu Phe Val Thr Lys Lys Ala Asn Ala Glu Glu Leu Ala
545                 550                 555                 560

Asn Asn Leu Lys Gln Glu Gly His Asn Leu Gly Leu Leu His Gly Asp
                565                 570                 575

Met Asp Gln Ser Glu Arg Asn Lys Val Ile Ser Asp Phe Lys Lys Lys
                580                 585                 590

Asp Ile Pro Val Leu Val Ala Thr Asp Val Ala Ala Arg Gly Leu Asp
                595                 600                 605

Ile Pro Ser Ile Lys Thr Val Ile Asn Tyr Asp Val Ala Arg Asp Ile
                610                 615                 620

Asp Thr His Thr His Arg Ile Gly Arg Thr Gly Arg Ala Gly Glu Lys
625                 630                 635                 640

Gly Val Ala Tyr Thr Leu Leu Thr Pro Lys Asp Ser Asn Phe Ala Gly
                645                 650                 655

Asp Leu Val Arg Asn Leu Glu Gly Ala Asn Gln His Val Ser Lys Glu
                660                 665                 670

Leu Leu Asp Leu Ala Met Gln Asn Ala Trp Phe Arg Lys Ser Arg Phe
                675                 680                 685

Lys Gly Gly Lys Gly Lys Lys Leu Asn Ile Gly Gly Gly Leu Gly
                690                 695                 700

Tyr Arg Glu Arg Pro Gly Leu Gly Ser Glu Asn Met Asp Arg Gly Asn
705                 710                 715                 720

Asn Asn Val Met Ser Asn Tyr Glu Ala Tyr Lys Pro Ser Thr Gly Ala
                725                 730                 735

Met Gly Asp Arg Leu Thr Ala Met Lys Ala Ala Phe Gln Ser Gln Tyr
                740                 745                 750

Lys Ser His Phe Val Ala Ala Ser Leu Ser Asn Gln Lys Ala Gly Ser
                755                 760                 765

Ser Ala Ala Gly Ala Ser Gly Trp Thr Ser Ala Gly Ser Leu Asn Ser
                770                 775                 780

Val Pro Thr Asn Ser Ala Gln Gln Gly His Asn Ser Pro Asp Ser Pro
785                 790                 795                 800
```

-continued

Val Thr Ser Ala Ala Lys Gly Ile Pro Gly Phe Gly Asn Thr Gly Asn
            805                 810                 815

Ile Ser Gly Ala Pro Val Thr Tyr Pro Ser Ala Gly Ala Gln Gly Val
            820                 825                 830

Asn Asn Thr Ala Ser Gly Asn Asn Ser Arg Glu Gly Thr Gly Gly Ser
            835                 840                 845

Asn Gly Lys Arg Glu Arg Tyr Thr Glu Asn Arg Gly Ser Ser Arg His
    850                 855                 860

Ser His Gly Glu Thr Gly Asn Arg His Ser Asp Ser Pro Arg His Gly
865                 870                 875                 880

Asp Gly Gly Arg His Gly Asp Gly Tyr Arg His Pro Glu Ser Ser Ser
            885                 890                 895

Arg His Thr Asp Gly His Arg His Gly Glu Asn Arg His Gly Gly Ser
            900                 905                 910

Ala Gly Arg His Gly Glu Asn Arg Gly Ala Asn Asp Gly Arg Asn Gly
            915                 920                 925

Glu Ser Arg Lys Glu Ala Phe Asn Arg Glu Gly Lys Met Glu Pro Lys
            930                 935                 940

Met Glu Pro Lys Ala Asp Ser Ser Lys Met Asp Lys Val Asp Ser Lys
945                 950                 955                 960

Thr Asp Lys Thr Ala Asp Gly Phe Ala Val Pro Glu Pro Pro Lys Arg
            965                 970                 975

Lys Lys Gly Arg Trp Asp Ser Arg Gly Cys Ala Lys Ala Asn Gln Leu
            980                 985                 990

Ser Leu Ile Phe Arg Lys Ile Leu Val Thr Arg Cys Leu Arg Ala Gly
            995                1000                1005

Leu Gly Ser Lys Val Gly Pro Pro Ala Leu Ser Gly Glu Leu Glu Leu
    1010                1015                1020

Gly Asp Ile Thr Pro Ser Ser Glu Gly Ile Phe Gly Cys Phe Leu Gly
1025                1030                1035                1040

Lys Leu Phe Trp Ser Leu Glu Ala Val Arg Ala Gly Lys Leu Leu Leu
            1045                1050                1055

Ala Leu Gly Glu Leu Ser Cys Gly Val Glu Val Ile Leu Gly Arg Val
            1060                1065                1070

Phe Gly Thr Lys Leu Thr Leu Gly Leu Tyr Tyr Met Leu Ile Phe Phe
            1075                1080                1085

Thr Lys Val Ser Pro Tyr Lys His Leu Ile Glu Phe Phe Leu Val
            1090                1095                1100

Val Trp Pro Gly Ser Pro His Phe Arg Ser Trp Leu Leu Gln Ile Gln
1105                1110                1115                1120

Ser Ile Glu Leu Thr Val Gly Glu Gln Phe Gly Ser Cys Arg His Leu
            1125                1130                1135

Gln Gly Arg Glu Met Ser Asp Ser Lys Trp Glu Leu Met Leu Arg Ser
            1140                1145                1150

Pro Ala Arg Phe Ala Ser Ser Pro Glu Thr Cys Arg Lys His Leu Ser
            1155                1160                1165

Asp Pro Gly Ser Glu Asp Ser Gln Lys Pro Gln Gly Leu Lys Gly Lys
            1170                1175                1180

Gly Asp Pro Gly Asn Cys Ser Arg Ile Ala Pro Gly Leu Arg Trp Tyr
1185                1190                1195                1200

Cys Ile Asn Thr Arg Asp Pro Thr Thr Ala Phe Lys Val Ser Ser Ile
            1205                1210                1215

-continued

```
Ser Leu Tyr Phe Phe Leu Ala Pro Met Ile Glu Lys Ser Phe Ala Glu
            1220                1225                1230

Met Ile Leu Met Ile Phe Val Tyr Arg Leu Lys Gly Lys Glu Ile Lys
            1235                1240                1245

Lys Lys Lys Lys Lys Lys Lys Ala Ala Ala Glu Phe
        1250                1255            1260

<210> SEQ ID NO 5
<211> LENGTH: 25
<212> TYPE: DNA
<213> ORGANISM: human

<400> SEQUENCE: 5
tgctcatgga agcataagca gccac                                          25

<210> SEQ ID NO 6
<211> LENGTH: 25
<212> TYPE: DNA
<213> ORGANISM: human

<400> SEQUENCE: 6
caccgacgaa tacgaaggta ctcgt                                          25
```